(12) United States Patent
Barras et al.

(10) Patent No.: US 12,404,531 B2
(45) Date of Patent: Sep. 2, 2025

(54) METHOD FOR PURIFYING (−)-Ambrox

(71) Applicant: Givaudan SA, Vernier (CH)

(72) Inventors: Jean-Pierre Barras, Genèva (CH);
Sylvie Morel, Prévessin-Moens (FR);
Eric Eichhorn, Zürich (CH)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 18/018,360

(22) PCT Filed: Jul. 29, 2021

(86) PCT No.: PCT/EP2021/071246
§ 371 (c)(1),
(2) Date: Jan. 27, 2023

(87) PCT Pub. No.: WO2022/023464
PCT Pub. Date: Feb. 3, 2022

(65) Prior Publication Data
US 2023/0212624 A1    Jul. 6, 2023

(30) Foreign Application Priority Data
Jul. 30, 2020  (GB) ........................... 2011823

(51) Int. Cl.
*C12P 17/04*    (2006.01)
*C12N 9/90*    (2006.01)

(52) U.S. Cl.
CPC ............ *C12P 17/04* (2013.01); *C12N 9/90* (2013.01); *C12Y 504/99017* (2013.01)

(58) Field of Classification Search
CPC .. C12P 17/04; C12P 7/40; A47L 13/17; C12Y 504/99017; B01D 61/58
USPC ........................................ 435/126
See application file for complete search history.

(56) References Cited

U.S. PATENT DOCUMENTS

| | | |
|---|---|---|
| 5,274,134 A | 12/1993 | Bruns et al. |
| 5,670,670 A | 9/1997 | Knuebel et al. |

FOREIGN PATENT DOCUMENTS

| | | |
|---|---|---|
| EP | 0165458 A2 | 12/1985 |
| EP | 0550889 A1 | 7/1993 |
| WO | 2010092872 A1 | 8/2010 |
| WO | 2016170099 A1 | 10/2016 |
| WO | 2016170106 A1 | 10/2016 |
| WO | 2017182542 A1 | 10/2017 |
| WO | 2018154048 A1 | 8/2018 |
| WO | 2018157021 A1 | 8/2018 |

OTHER PUBLICATIONS

International Search Report for App. No. PCT/EP2021/071246 dated Dec. 3, 2021.
Written Opinion for App. No. PCT/EP2021/071246 dated Dec. 3, 2021.
Great Britain Search Report for App. No. 2011823.8 dated Jan. 26, 2021.
Eric Eichhorn, et al., Biocatalytic Process for (−)-Ambrox Production Using Squalene Hopene Cyclase, Advanced Synthesis and Catalysis, May 2, 2018, pp. 2239-2251, vol. 360, Wiley-VCH Verlag Gmbh & Co. KGaA.

*Primary Examiner* — Tekchand Saidha
*Assistant Examiner* — Mohammad Y Meah
(74) *Attorney, Agent, or Firm* — Curatolo Sidoti & Trillis Co., LPA; Floyd Trillis, III; Salvatore A. Sidoti

(57) ABSTRACT

A method for purifying a crude flavor or perfumery or cosmetic ingredient or intermediate, for example crude (−)-Ambrox, comprising a number of washing steps, the products of said method, and uses of said product.

10 Claims, 1 Drawing Sheet
Specification includes a Sequence Listing.

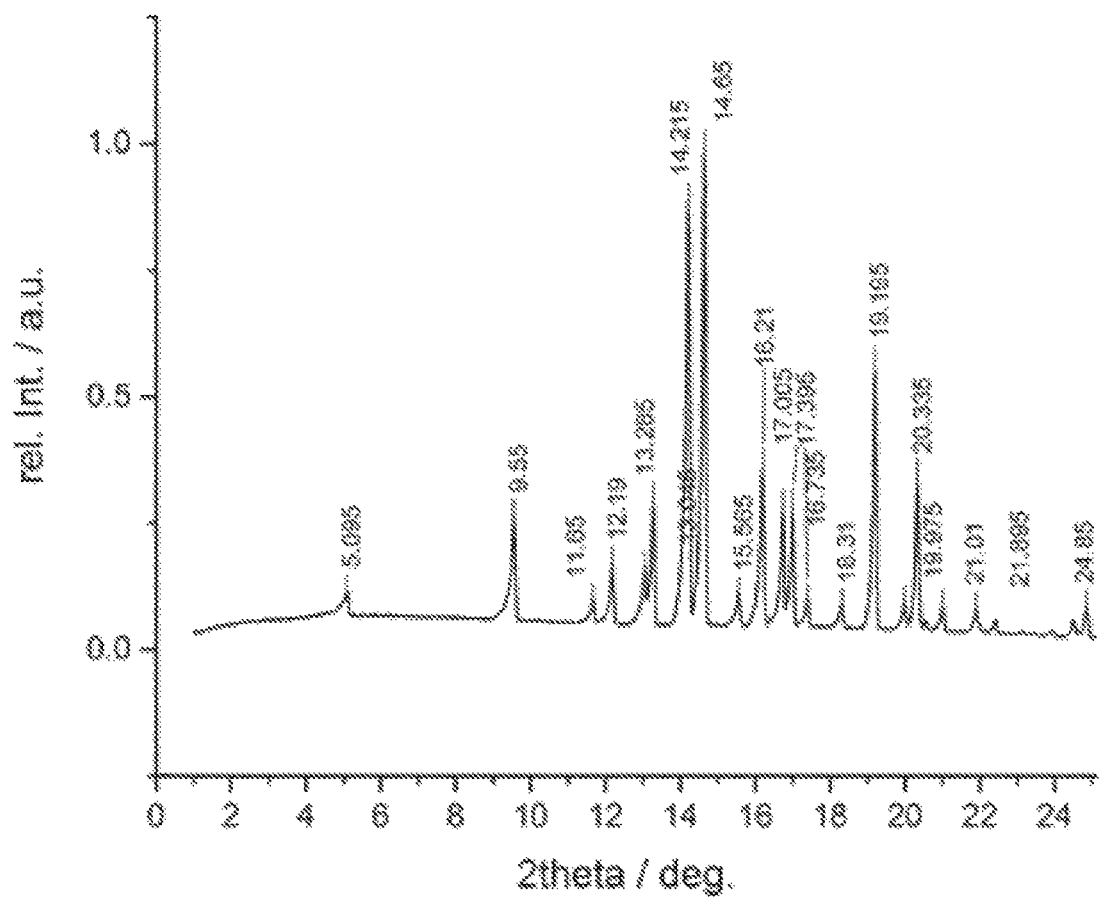

SEQUENCE LISTING

<160> NUMBER OF SEQ ID NOS: 1

<210> SEQ ID NO 1
<211> LENGTH: 631
<212> TYPE: PRT
<213> ORGANISM: Alicyclobacillus acidocaldarius

<400> SEQUENCE: 1

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
          20                  25                  30

Trp Gly Pro Leu Leu Ser Asn Val Thr Met Glu Ala Glu Tyr Val Leu
         35                  40                  45

Leu Cys His Ile Leu Asp Arg Val Asp Arg Asp Arg Met Glu Lys Ile
 50                  55                  60

Arg Arg Tyr Leu Leu His Glu Gln Arg Glu Asp Gly Thr Trp Ala Leu
 65              70                  75                  80

Tyr Pro Gly Gly Pro Pro Asp Leu Asp Thr Thr Ile Glu Ala Tyr Val
                 85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
            115                 120                 125

Phe Thr Arg Met Trp Leu Ala Leu Val Gly Glu Tyr Pro Trp Glu Lys
        130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
            195                 200                 205

Gly Ala Lys Gly Gly Gly Gly Trp Ile Phe Asp Ala Leu Asp Arg Ala
        210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
        370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

-continued

```
Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
        610                 615                 620

Lys Gln Ala Ile Glu Arg Arg
625                 630
```

METHOD FOR PURIFYING (−)-Ambrox

CROSS REFERENCE TO RELATED APPLICATIONS

This application is a national stage application of International Application No. PCT/EP2021/071246, filed 29 Jul. 2021, which claims priority from Great Britain Patent Application No. 2011823.8, filed 30 Jul. 2020, both of which applications are incorporated herein by reference.

SEQUENCE LISTING

Attached to this application is a Sequence Listing as filed in the International application. The Sequence Listing includes a sequence for SEQ ID NO: 1. Please add the Sequence Listing to the present application.

TECHNICAL FIELD

The present invention relates generally to a method for purifying a crude flavor or perfumery or cosmetic ingredient or intermediate, in particular a method for purifying crude (−)-Ambrox. The present invention also relates to the product of this method and the various uses of said product.

BACKGROUND (−)-Ambrox of formula (I) below is a commercially important perfumery ingredient,

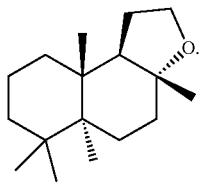

(I)

(−)-Ambrox is known commercially as Ambrox (Firmenich), Ambroxan (Henkel), Ambrofix (Givaudan), Amberlyn (Quest), Cetalox Laevo (Firmenich), Ambermor (Aromor) and/or Norambrenolide Ether (Pacific).

The (−)-Ambrox enantiomer rather than the (+)-Ambrox enantiomer provides the special desirable sensory benefits. The odour of the (−)-Ambrox enantiomer is described as musk-like, woody, warm or ambery whereas the (+)-Ambrox enantiomer has a relatively weak odour note.

WO 2017/182542, the contents of which are incorporated herein by reference, discloses a method for preparing (−)-Ambrox by bioconversion of a 7E,3E/Z-homofarnesol mixture. Example 4 of WO 2017/182542 discloses a downstream process for purifying (−)-Ambrox comprising a heating step (wherein the bioconversion broth is heated to a temperature of about 80-85° C. for a period of about 15 minutes to inactivate the biocatalyst), after which liquid (−)-Ambrox is cooled to a temperature of about 20° C. where it crystallizes again. The (−)-Ambrox crystals are separated from the bioconversion broth by filtration and washed with water on the filter to remove the bioconversion broth leftovers. Upgrading the so obtained crude (−)-Ambrox to the desired chemical and olfactory quality requires a number of successive steps, which include dissolving the crystals in ethanol, clarifying and then bleaching the so obtained solution before finally re-crystallizing the (−)-Ambrox. This is a complex and labour intensive process which uses multiple items of equipment. This process also uses flammable ethanol which has to be safely and correctly handled and, at the end of the process, either disposed of or upgraded for reuse.

It is therefore desirable to provide new and improved methods for purifying (−)-Ambrox. In particular it is desirable to provide methods for simplifying the purification of (−)-Ambrox, for example by using less equipment, avoiding re-crystallization, and avoiding the production of (−)-Ambrox containing mother liquor concentrates which have to be reworked.

The same considerations are also applicable for the preparation of other perfumery ingredients and intermediates, crude flavor ingredients and intermediates, and crude cosmetic ingredients and intermediates, in particular perfumery ingredients and intermediates and crude flavor ingredients and intermediates in crystalline form made by a bioconversion reaction, for example using a SHC/HAC enzyme or other biocatalyst.

SUMMARY

In accordance with a first aspect of the present invention there is provided a method for purifying a crude flavor or perfumery or cosmetic ingredient or intermediate, the method comprising:
washing with an aqueous acid;
washing with an aqueous surfactant; and
optionally washing with an aqueous alkali.

In accordance with a particular embodiment of the first aspect of the present invention there is provided a method for purifying crude (−)-Ambrox, the method comprising:
washing with an aqueous acid;
washing with an aqueous surfactant; and
optionally washing with an aqueous alkali.

The washing steps of the first aspect of the present invention may take place in any order suitable to purify the crude flavor or perfumery or cosmetic ingredient or intermediates, for example the crude (−)-Ambrox.

In accordance with a particular embodiment of the first aspect of the present invention there is provided a method for purifying a crude flavor or perfumery or cosmetic ingredient or intermediate, the method comprising:
(a) washing the crude flavor or perfumery or cosmetic ingredient or intermediate with an aqueous acid;
(b) washing the product of step (a) with an aqueous alkali;
(c) washing the product of step (b) with an aqueous surfactant.

In accordance with a particular embodiment of the first aspect of the present invention there is provided a method for purifying crude (−)-Ambrox, the method comprising:
(a) washing crude (−)-Ambrox with an aqueous acid;
(b) washing the product of step (a) with an aqueous alkali;
(c) washing the product of step (b) with an aqueous surfactant.

In accordance with a second aspect of the present invention there is provided a flavor or perfumery or cosmetic ingredient or intermediate obtained by or obtainable by the method of the first aspect of the present invention, including any embodiment thereof.

In accordance with a particular embodiment of the second aspect of the present invention there is provided (−)-Ambrox obtained by or obtainable by the method of the first aspect of the present invention, including any embodiment thereof.

In accordance with a third aspect of the present invention there is provided a use of the flavor or perfumery or cosmetic ingredient, for example (−)-Ambrox, of the second aspect of the present invention, including any embodiment thereof, as a flavor or perfumery or cosmetic ingredient.

In accordance with a fourth aspect of the present invention there is provided a perfume composition comprising the perfumery ingredient, for example (−)-Ambrox, of the second aspect of the present invention, including any embodiment thereof.

In accordance with a fifth aspect of the present invention there is provided a flavor composition comprising the flavor ingredient of the second aspect of the present invention, including any embodiment thereof.

In accordance with a sixth aspect of the present invention there is provided a cosmetic composition comprising the cosmetic ingredient of the second aspect of the present invention, including any embodiment thereof.

In accordance with a seventh aspect of the present invention there is provided a household care, a personal care, a laundry care, or an air care composition comprising a perfume composition of the fourth aspect of the present invention, including any embodiment thereof.

In accordance with a eighth aspect of the present invention there is provided a food or drink product comprising a flavor composition of the fifth aspect of the present invention, including any embodiment thereof.

In accordance with a ninth aspect of the present invention there is provided a cosmetic product comprising a cosmetic composition of the sixth aspect of the present invention, including any embodiment thereof.

In accordance with an tenth aspect of the present invention there is provided a Nutsche-type agitating and drying filter configured to purify a crude flavor or perfumery or cosmetic ingredient or intermediate by the method of the first aspect of the present invention, wherein the crude flavor or perfumery or cosmetic ingredient or intermediate comprises from about 20 wt % to about 30 wt % water based on the wet weight of the crude flavor or perfumery or cosmetic ingredient or intermediate.

In accordance with an eleventh aspect of the present invention there is provided a process for purifying a crude flavor or perfumery or cosmetic ingredient or intermediate, the process comprising washing the crude flavor or perfumery or cosmetic ingredient or intermediate in a Nutsche-type agitating and drying filter. The process may, for example, be in accordance with the method of the first aspect of the present invention, including any embodiment thereof.

Certain embodiments of the present invention may provide one or more of the following advantages, for example compared to the process described in WO 2017/182542:
- simpler process for purifying a crude flavor or fragrance or cosmetic ingredient or intermediate, for example crude (−)-Ambrox;
- cheaper process for purifying a crude flavor or fragrance or cosmetic ingredient or intermediate, for example crude (−)-Ambrox;
- less labor intensive process for purifying a crude flavor or fragrance or cosmetic ingredient or intermediate, for example crude (−)-Ambrox;
- greener and more environmentally friendly process;

The following advantages may be achieved even with a simpler, cheaper and less labor intensive process:
- reduction in the amount of equipment required to purify a crude flavor or fragrance or cosmetic ingredient or intermediate, for example crude (−)-Ambrox;
- avoids the need for re-crystallization;
- avoids or strongly reduces the use of ethanol;
- reduction of materials losses
- avoids the generation of a flavor or fragrance or cosmetic ingredient or intermediate, for example crude (−)-Ambrox, containing mother liquor concentrates which have to be reworked;
- high yielding process using fewer steps and requiring less time for purifying (−)-Ambrox (e.g. >95 mol % based on the crude starting material);
- production of (−)-Ambrox suitable for olfactory application;

The simpler, cheaper and less labor intensive process described herein may:
- remove or reduce insoluble and/or particulate materials;
- remove or reduce colored impurities;
- remove or reduce co-products of the bioconversion reaction;
- remove or reduce malodorous impurities.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise dearly contradicted by context.

BRIEF DESCRIPTION OF THE FIGURES

FIG. 1 shows an XRD pattern in which the scale of the abscissa is degrees 2-theta, and the ordinate is the intensity in counts.

DETAILED DESCRIPTION

There is provided herein a method for purifying a crude flavor or perfumery or cosmetic ingredient or intermediate, for example crude (−)-Ambrox, the method comprising:
washing with an aqueous acid;
washing with an aqueous surfactant; and
optionally washing with an aqueous alkali.

The washing steps of the first aspect of the present invention may take place in any order suitable to purify the crude flavor or perfumery or cosmetic ingredient or intermediate, for example the crude (−)-Ambrox. The washing steps each refer to washing of the crude flavor or perfumery or cosmetic ingredient or intermediate, for example the crude (−)-Ambrox, or the product of a previous washing step, which product may also be referred to as crude flavor or perfumery or cosmetic ingredient or intermediate, for example crude (−)-Ambrox.

For example, there is provided herein a method for purifying a crude flavor or perfumery or cosmetic ingredient or intermediate, the method comprising:
(a) washing the crude flavor or perfumery or cosmetic ingredient or intermediate with an aqueous acid;
(b) optionally washing the product of step (a) with an aqueous alkali; and
(c) washing the product of step (a), or the product of step (b) when present, with an aqueous surfactant.

For example, there is provided herein a method for purifying crude (−)-Ambrox, the method comprising:
(a) washing the crude (−)-Ambrox with an aqueous acid;
(b) optionally washing the product of step (a) with an aqueous alkali; and
(c) washing the product of step (a), or the product of step (b) when present, with an aqueous surfactant.

For example, there is provided herein a method for purifying a crude flavor or perfumery or cosmetic ingredient or intermediate, the method comprising:
(a) washing the crude flavor or perfumery or cosmetic ingredient or intermediate with an aqueous acid;
(b) washing the product of step (a) with an aqueous alkali; and
(c) washing the product of step (b) with an aqueous surfactant.

For example, there is provided herein a method for purifying crude (−)-Ambrox, the method comprising:
(a) washing the crude (−)-Ambrox with an aqueous acid;
(b) washing the product of step (a) with an aqueous alkali; and
(c) washing the product of step (b) with an aqueous surfactant.

For example, there is provided herein a method for purifying a crude flavor or perfumery or cosmetic ingredient or intermediate, the method comprising:
(a) washing the crude flavor or perfumery or cosmetic ingredient or intermediate with an aqueous surfactant;
(b) washing the product of step (a) with an aqueous acid; and
(c) optionally washing the product of step (b) with an aqueous alkali.

For example, there is provided herein a method for purifying crude (−)-Ambrox, the method comprising:
(a) washing the crude (−)-Ambrox with an aqueous surfactant;
(b) washing the product of step (a) with an aqueous acid; and
(c) optionally washing the product of step (b) with an aqueous alkali.

For example, there is provided herein a method for purifying a crude flavor or perfumery or cosmetic ingredient or intermediate, the method comprising:
(a) washing the crude flavor or perfumery or cosmetic ingredient or intermediate with a composition comprising aqueous acid and aqueous surfactant; and
(b) optionally washing the product of step (a) with an aqueous alkali.

For example, there is provided herein a method for purifying crude (−)-Ambrox, the method comprising:
(a) washing the crude (−)-Ambrox with a composition comprising aqueous acid and aqueous surfactant; and
(b) optionally washing the product of step (a) with an aqueous alkali.

There may be one or more further method steps, for example one or more further washing steps, before or after each of steps (a), (b) and/or (c) described herein. For example, the method may comprise washing with water one or more times before or after each of steps (a), (b) and/or (c). Where there are one or more further method steps before or after each of steps (a), (b) and/or (c), the "product of step (a)" refers to the product of step (a) and any further method steps carried out prior to performing step (b) and the "product of step (c)" refers to the product of step (b) and any further method steps carried out prior to performing step (c).

Crude Flavor or Perfumery or Cosmetic Ingredient or Intermediate Starting Material By "crude flavor or perfumery or cosmetic ingredient or Intermediate" it is meant a material comprising a perfumery ingredient or an intermediate to a perfumery ingredient or a flavor ingredient or an intermediate to a flavor ingredient or a cosmetic ingredient or an intermediate to a cosmetic ingredient, and impurities.

As used herein, the term "perfumery ingredient" refers to a compound that can be used in a composition to provide a desirable odor.

As used herein, the term "flavor ingredient" refers to a compound that can be used in a composition to provide a desirable taste.

As used herein, the term "cosmetic ingredient" refers to a compound that can be used as an active ingredient in a cosmetic composition to provide a desirable appearance when applied to a subject (e.g. a human subject), particularly the skin of a subject. This may include natural products which may, for example, be crystalline.

As used herein, the term "perfumery intermediate" refers to a compound that can be used to prepare a perfumery ingredient.

As used herein, the term "flavor Intermediate" refers to a compound that can be used to prepare a flavor ingredient.

As used herein, the term "cosmetic intermediate" refers to a compound that can be used to prepare a cosmetic ingredient.

As used herein, the term "impurities" refers to any solid or liquid materials that are not the flavor or perfumery or cosmetic ingredient or intermediate itself. This includes, for example, unreacted starting materials for the production of the flavor or perfumery or cosmetic ingredient or intermediate, by-products of the reaction that produces the flavor or perfumery or cosmetic ingredient or intermediate, particulate materials, cells, cell debris, and various impurities that are insoluble in solvents such as water, water-miscible solvents and organic solvents, for example impurities that are insoluble in ethanol such as precipitated mineral salts and proteins.

Therefore, by "purifying a flavor or perfumery or cosmetic ingredient or intermediate", it is meant a method that removes and reduces the amount of impurities in the crude flavor or perfumery or cosmetic ingredient or intermediate.

The crude flavor or perfumery or cosmetic ingredient or intermediate may, for example, be in solid form.

The crude flavor or perfumery or cosmetic ingredient or intermediate may, for example, be in crystalline form.

The crude flavor or perfumery or cosmetic ingredient or intermediate may have been prepared by a bioconversion process, for example using a squalene hopene cyclase/Homofarnesol Ambrox Cyclase (SHC/HAC) enzyme. The purification methods described herein may therefore further comprise the step of preparing the crude flavor or perfumery or cosmetic ingredient or intermediate by a bioconversion process prior to the purification steps described herein. The bioconversion broth resulting from a bioconversion process, for example as described herein, may generally comprise a solid phase containing the flavor or perfumery or cosmetic ingredient or intermediate and a liquid phase or phases containing water and/or an oily phase, for example that may contain residual unreacted starting material and other oily or oil-soluble impurities or by-products.

The term "crude flavor or perfumery or cosmetic ingredient or Intermediate" may refer to the material that is separated from the bioconversion broth in a pre-purification step (e.g. by filtration) prior to the purification method described herein.

The presently described purification methods may, for example, work particularly well with products in solid form where impurities are deposited on the surface of the product. This may mean that they can be easily removed by the washing steps described herein.

The reaction conditions for making the crude flavor or perfumery or cosmetic ingredient or intermediate and any pre-purification steps may, for example, be in accordance with the method and pre-purification steps described herein in relation to crude (−)-Ambrox starting material (but using the correct starting materials).

The crude flavor or perfumery or cosmetic ingredient or intermediate may, for example, be selected from (−)-Ambrox, (−)-Ambra-oxide, 3a-ethyl-6,6,9a-trimethyldodecahydronaphtho([2,1-b]furan and (+)-Amberketal. In particular, the crude flavor or perfumery ingredient or intermediate may be (−)-Ambrox.

Crude (−)-Ambrox Starting Material

By "crude (−)-Ambrox" it is meant a material comprising (−)-Ambrox and impurities. As used herein, the term "impurities" refers to any solid or liquid materials that are not (−)-Ambrox. This includes, for example, unreacted starting materials for the production of the (−)-Ambrox (e.g. homofarnesol), by-products of the reaction that produces the (−)-Ambrox (e.g. compounds of formula (II), (III) and/or (IV) as described in Table 2 herein), particulate materials, cells, cell debris, and various impurities that are insoluble in solvents such as water, water-miscible solvents and organic solvents, for example impurities that are insoluble in ethanol such as precipitated mineral salts and proteins.

Therefore, by "purifying (−)-Ambrox", it is meant a method that removes and reduces the amount of impurities in the crude (−)-Ambrox.

The crude (−)-Ambrox may have been prepared by a bioconversion process using a squalene hopene cyclase/Homofarnesol Ambrox Cyclase (SHC/HAC) enzyme to convert homofarnesol to (−)-Ambrox (see further details below). The bioconversion broth resulting from a bioconversion process, for example as described herein, may generally comprise a solid phase containing (−)-Ambrox and a liquid phase or phases containing water and/or an oily phase that may contain residual unreacted homofarnesol and other oily or oil-soluble impurities or by-products. For example some compounds of formula (II), (III) and (IV) may be present in such an oily phase.

The term "crude (−)-Ambrox" may refer to the material that is separated from the bioconversion broth in a pre-purification step (e.g. by filtration) prior to the purification method described herein.

The solid phase (including (−)-Ambrox) obtained from the bioconversion process may be separated from the liquid phase of the bioconversion broth by filtration, such as centrifugal filtration, or decantation/sedimentation. By selecting a filter with an appropriate mesh size, it is also possible to separate the solid form of (−)-Ambrox from particulate material present in the bioconversion broth, for example cells or cell debris. Decantation/sedimentation, similar to filtration, exploits the difference in particle size and/or particle mass between the particulate matter and the solid form of (−)-Ambrox to allow their separation, the former remaining suspended in supernatant, which can be discarded, whilst the latter can be isolated as a sediment, to be recovered and subjected to purification steps. Suitable methods for isolating (−)-Ambrox from bioconversion broth including cell debris are described in WO 2017/182542 and VO 2016/170108, the contents of which are incorporated herein by reference. For example, the biocatalyst may first be inactivated by heating or by increasing the pH of the bioconversion broth to about 10-11 (alkalinisation). Cells, cell debris, insoluble materials and/or other particulate materials can then be removed from the (−)-Ambrox by physical means such as filtration. This can have a deodorizing effect because cells and/or cell debris and/or insoluble materials and/or other particulate materials that stick to (−)-Ambrox may be the cause of unpleasant off-notes if they remain in the crude (−)-Ambrox product.

The biocatalyst may, for example, be inactivated by increasing the temperature of the bioconversion broth. The temperature may be increased to a temperature that is high enough to inactivate the bacteria but is below the melting point of (−)-Ambrox (i.e. below about 75-80° C.). The (−)-Ambrox therefore does not turn to liquid. Rather, at this temperature (e.g. about 50° C. to about 60° C. such as about 55° C.), (−)-Ambrox slightly dissolves and the average crystal size is reduced. The crystals then grow again during the cooling phase. This helps them to be separated from the liquid phase of the bioconversion broth by filtration.

For example, the temperature of the bioconversion broth may be increased to a temperature in the range of about 50° C. to about 60° C. For example, the temperature of the bioconversion broth may be increased to a temperature in the range of about 52° C. to about 58° C. or from about 54° C. to about 56° C. For example, the temperature of the bioconversion broth may be increased to a temperature of about 55° C.

Alternatively, the biocatalyst may be inactivated by increasing the pH of the bioconversion broth to about 10-11, for example using sodium hydroxide. This may, for example, reduce the energy consumption and loss of time when compared to inactivating the biocatalyst by heating, reduce flocculation (which may hinder filtration), reduce malodor issues, and/or leave mainly mineral impurities that are insoluble in ethanol, which may be eliminated by filtration.

The crude (−)-Ambrox that undergoes the purification methods described herein may therefore be substantially or completely free of intact cells following the biocatalyst inactivation.

After the (−)-Ambrox is separated from the particulate materials of the bioconversion broth (e.g. by filtration), any aqueous material present in the crude (−)-Ambrox may be residuals from the broth in which the cells had been originally cultivated. The crude (−)-Ambrox may, for example, undergo a further pre-purification washing step using water prior to the purification method described herein. After the additional pre-purification washing step with water, any aqueous material present in the crude (−)-Ambrox may be water.

The crude (−)-Ambrox may, for example, comprise equal to or less than about 99 wt % of (−)-Ambrox based on the dry content of the crude (−)-Ambrox. For example, the crude (−)-Ambrox may comprise equal to or less than about 98 wt % or equal to or less than about 97 wt % or equal to or less than about 95 wt % or equal to or less than about 95 wt % of (−)-Ambrox based on the dry content of the crude (−)-Ambrox.

The crude (−)-Ambrox may, for example, comprise equal to or greater than about 80 wt % of (−)-Ambrox based on the dry content of the crude (−)-Ambrox. For example, the crude (−)-Ambrox may comprise equal to or greater than about 81 wt % or equal to or greater than about 82 wt % or equal to or greater than about 83 wt % or equal to or greater than about 84 wt % or equal to or greater than about 85 wt % or equal to or greater than about 86 wt % or equal to or greater than about 87 wt % or equal to or greater than about 88 wt % or equal to or greater than about 89 wt % or equal to or greater than about 90 wt % or equal to or greater than about 91 wt % or equal to or greater than about 92 wt % or equal to or greater than about 93 wt % or equal to or greater than about 94 wt % or equal to or greater than about 95 wt % of (−)-Ambrox based on the dry content of the crude (−)-Ambrox.

For example, the crude (−)-Ambrox may comprise from about 80 wt % to about 99 wt % or from about 85 wt % to about 97 wt % or from about 90 wt % to about 95 wt % or from about 93 wt % to about 97 wt % of (−)-Ambrox based on the dry content of the crude (−)-Ambrox.

The crude (−)-Ambrox may, for example, comprise equal to or greater than about 1 wt % total impurities based on the dry content of the crude (−)-Ambrox. For example, the crude (−)-Ambrox may comprise equal to or greater than about 2 wt % or equal to or greater than about 3 wt % or equal to or greater than about 4 wt % or equal to or greater than about 5 wt % total impurities based on the dry content of the crude (−)-Ambrox.

The crude (−)-Ambrox may, for example, comprise equal to or less than about 20 wt % total impurities based on the dry content of the crude (−)-Ambrox. For example, the crude (−)-Ambrox may comprise equal to or less than about 19 wt % or equal to or less than about 18 wt % or equal to or less than about 17 wt % or equal to or less than about 16 wt % or equal to or less than about 15 wt % or equal to or less than about 14 wt % or equal to or less than about 13 wt % or equal to or less than about 12 wt % or equal to or less than about 11 wt % or equal to or less than about 10 wt % or equal to or less than about 9 wt % or equal to or less than about 8 wt % or equal to or less than about 7 wt % or equal to or less than about 6 wt % total impurities based on the dry content of the crude (−)-Ambrox.

For example, the crude (−)-Ambrox may comprise from about 1 wt % to about 20 wt % or from about 2 wt % to about 15 wt % or from about 3 wt % to about 10 wt % total impurities based on the dry content of the crude (−)-Ambrox.

The dry content of the crude (−)-Ambrox is the material remaining after water content has been deducted. For example, a water content of 25% measured by Karl-Fischer titration equates to a dry content of 75%. The dry content is solid but a small amount of oily residue may be present. The oily residue may, for example, be one or more compounds of formula (II), (III) and/or (IV) as described in Table 2 herein or any unreacted homofarnesol.

The crude (−)-Ambrox may, for example, comprise water. Alternatively, the crude (−)-Ambrox may be dry (i.e. not comprise any water). It may be advantageous to remove water from the crude (−)-Ambrox to avoid bacterial growth and production of off-notes in the crude material.

The crude (−)-Ambrox may, for example, comprise equal to or greater than about 2 wt % water based on the total wet weight of the crude (−)-Ambrox. For example, the crude (−)-Ambrox may comprise equal to or greater than about 5 wt % or equal to or greater than about 10 wt % or equal to or greater than about 15 wt % or equal to or greater than about 20 wt % water based on the total wet weight of the crude (−)-Ambrox.

The crude (−)-Ambrox may, for example, comprise equal to or less than about 50 wt % water based on the total wet weight of the crude (−)-Ambrox. For example, the crude (−)-Ambrox may comprise equal to or less than about 45 wt % or equal to or less than about 40 wt % or equal to or less than about 35 wt % or equal to or less than about 30 wt % or equal to or less than about 25 wt % or equal to or less than about 20 wt % water based on the total wet weight of the crude (−)-Ambrox.

For example, the crude (−)-Ambrox may comprise from about 2 wt % to about 50 wt % or from about 10 wt % to about 25 wt % or from about 20 wt % to about 25 wt % water based on the total wet weight of the crude (−)-Ambrox.

The crude (−)-Ambrox may, for example, comprise equal to or greater than about 50 wt % total dry content based on the total wet weight of the crude (−)-Ambrox. For example, the crude (−)-Ambrox may comprise equal to or greater than about 55 wt % or equal to or greater than about 60 wt % or equal to or greater than about 65 wt % or equal to or greater than about 70 wt % total dry content based on the total wet weight of the crude (−)-Ambrox.

The crude (−)-Ambrox may, for example, comprise equal to or less than about 100 wt % or equal to or less than about 99 wt % or equal to or less than about 98 wt % or equal to or less than about 95 wt % or equal to or less than about 90 wt % or equal to or less than about 85 wt % or equal to or less than about 80 wt % or equal to or less than about 75 wt % total dry content based on the total wet weight of the crude (−)-Ambrox.

For example, the crude (−)-Ambrox may comprise from about 50 wt % to about 100 wt % or from about 60 wt % to about 98 wt % or from about 70 wt % to about 95 wt % or from about 75 wt % to about 90 wt % total dry content based on the total wet weight of the crude (−)-Ambrox.

For example, the crude (−)-Ambrox may comprise from about 70 wt % to about 75 wt % dry materials and from about 20 wt % to about 25 wt % water. The dry materials in the crude (−)-Ambrox may comprise from about 5 wt % to about 10 wt % impurities.

The method described herein is particularly suitable for purifying crude (−)-Ambrox made by a bioconversion process using a squalene hopene cycase/Homofarnesol Ambrox Cycase (SHC/HAC) enzyme to convert E,E-homofarnesol to (−)-Ambrox. The term "SHC/HAC enzyme" includes both wild-type SHC/HAC enzymes and variants of wild-type SHC/HAC enzymes. Suitable methods for preparing (−)-Ambrox by a biocatalytic process using SHC enzymes are described, for example, in VO 2016/170106, VO 2016/170099, WO 2017/182542, WO 201/157021, and Eichhorn et al. (2018), Adv. Synth. Catal., 360: 2339-2351, the contents of which are incorporated herein by reference. Any suitable bioconversion method may be used to make the crude (−)-Ambrox. Suitable SHC/HAC enzymes include but are not limited to those disclosed in Tables 13 and 14 of WO 2016/170099, for example the SHC/HAC enzyme 215G2 SHC.

The crude (−)-Ambrox may be made by a method comprising culturing host cells to produce an SHC/HAC enzyme and contacting the host cells and/or SHC/HAC enzyme produced by the host cells with 3E,7E-homofarnesol under conditions suitable to promote the conversion of 3E,7E-homofarnesol to (−)-Ambrox.

The host cells may be cultured to create a sufficient biocatalyst, harvested and washed (and optionally stored (e.g. refrigerated, frozen or lyophilized)) before starting the bioconversion step.

In certain embodiments, the (−)-Ambrox is in a solid form as described in VO 2016/170106, WO 2016/170099, and/or VO 2017/182542, the contents of which are incorporated herein by reference.

Due to its very low solubility in water, (−)-Ambrox crystallizes in the broth during the bioconversion process. This occurs as soon as the E,E-homofarnesol conversion rate exceeds about 50%.

In certain embodiments, no re-crystallization steps (i.e. steps comprising solubilizing (−)-Ambrox crystals and then re-crystallizing the (−)-Ambrox) are required following the bioconversion reaction in order to purify the crude (−)-Ambrox (i.e. after the first crystallization during the bioconversion process).

Homofarnesol may have isomerism as shown below.

TABLE 1

Homofarnesol isomers

| Compound | Abbreviation | Name and Structure |
|---|---|---|
| E,E-Homofarnesol | EEH | 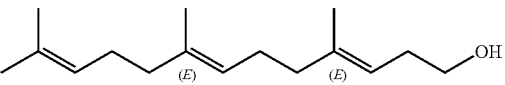 [SMILES: CC(C)=CCC/C(C)=C/CC/C(C)=C/CCO]<br>(3E,7E)-4,8,12-trimethyltrideca-3,7,11-trien-1-ol |
| E,Z-Homofarnesol | EZH | 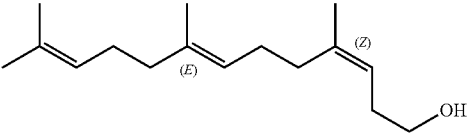 [SMILES: CC(C)=CCC/C(C)=C/CC/C(C)=C\CCO]<br>(3Z,7E)-4,8,12-trimethyltrideca-3,7,11-trien-1-ol |
| Z,E-Homofarnesol | ZEH | 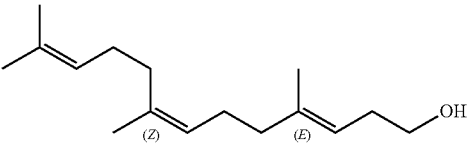 [SMILES: CC(C)=CCC/C(C)=C\CC/C(C)=C/CCO]<br>(3E,7Z)-4,8,12-trimethyltrideca-3,7,11-trien-1-ol |
| Z,Z-Homofarnesol | ZZH | 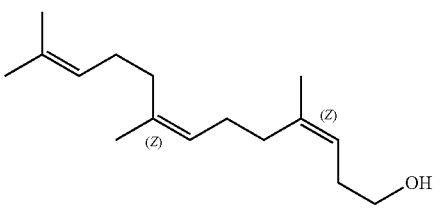 [SMILES: CC(C)=CCC/C(C)=C\CC/C(C)=C\CCO]<br>(3Z,7Z)-4,8,12-trimethyltrideca-3,7,11-trien-1-ol |

Whilst homofarnesol may be present as a mixture of our isomers, the (3Z,7Z), (3E,7Z), (3Z,7E) and (3E,7E) isomers, FIG. 12 of WO 2016/170099 shows the reaction products produced ((−)-Ambrox and compound (IV)) when EEH is used as a starting material (for bioconversion with wild-type SHC/HAC and/or a SHC/HAC variant), and the reaction products produced ((−)-Ambrox and compounds (II), (III) and (IV) (see Table 2)) when EE:EZ is used as a starting material. For ease of reference, compounds (1) to (IV) are identified In Table 2 below. Scheme 2 of Eichhorn et al. (2018), Adv. Synth. Catal., 360: 2339-2351, also demonstrates that the (E,Z) isomer (corresponding to the 3Z 7E homofarnesol isomer) only produces compounds (II) and (III) but not (−)-Ambrox.

As used herein, a reference to (3E,7E)-homofarnesol is a reference to E,E-homofarnesol which is also designated as EEH.

The starting materials for the processes described herein for preparing (−)-Ambrox may, for example, be (3E,7E)-homofarnesol or a mixture comprising (3E,7E)-homofarnesol, for example a mixture of isomers of homofarnesol comprising (3E,7E)-homofarnesol.

Preferably the homofarnesol starting material comprises a mixture of (3E,7E) and (3Z,7E), termed herein an EE:EZ isomeric mixture. An EE:EZ isomeric mixture of homofarnesol has the CAS number of 35826-67-6.

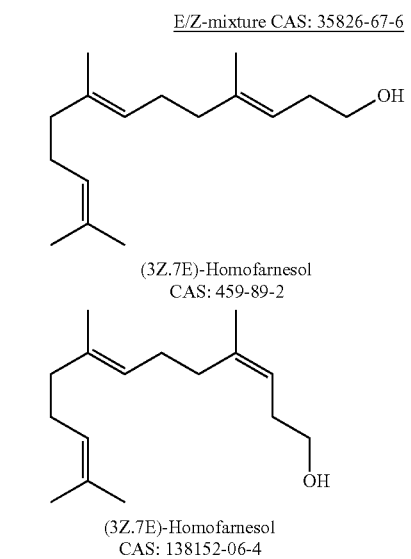

For example, the weight ratio of EEH:EZH is about 100:00; 99:01; 98:02; 97:03; 96:04; 95:05; 94:06; 93:07; 92:08; 91:09; 90:10; 89:11; 88:12; 87:13; 86:14; 85:15; 84:16; 83:17; 82:18; 81:19; 80:20; 79:21; 78:22; 77:23; 76:24; 75:25; 74:26; 73:27; 72:28; 71:29; 70:30; 69:31: 68:32; 67:33; 66:34; 65:35; 64:36; 63:37; 62:38; 61:39; 60:40; 59:41; 58:42; 57:43; 56:44; 55:45; 54:46; 53:47:

52:48; 51:49; or about 50:50. For example, the homofarnesol starting material comprises an EE:EZ weight ratio of 88:14. For example, the homofarnesol starting material comprises an EE:EZ weight ratio of 80:20.

The number of homofarnesol isomers present may influence the speed of the reaction. A SHC/HAC enzyme may be capable of converting E,E-homofarnesol to (−)-Ambrox from a complex mixture of homofarnesol isomers (e.g. EE:EZ:ZE:ZZ). However, a lower conversion rate may be observed, which is consistent with the view that homofarnesol isomers other than EEH may compete with EEH for access to the SHC/HAC enzyme active site and thus may act as competitive inhibitors for the conversion of EEH to (−)-Ambrox and/or also act as alternative substrates (see for example, Eichhorn et al (2018) Adv. Synth. Catal. 360: 2339-2351, the contents of which are incorporated here by reference). Accordingly, the homofarnesol substrate may comprise an isomeric mixture of 2-4 isomers, preferably two isomers.

The homofarnesol (e.g. EEH) starting material may not all be converted to (−)-Ambrox or a by-product of the reaction. Any unreacted homofarnesol may, for example, be removed by filtration prior to the purification of the crude (−)-Ambrox. However, crude (−)-Ambrox may comprise small amounts of homofarnesol (e.g. EEH).

For example, crude (−)-Ambrox may comprise equal to or greater than about 0.05 wt % homofarnesol. For example, crude (−)-Ambrox may comprise equal to or greater than about 0.1 wt % or equal to or greater than about 0.5 wt % or equal to or greater than about 1 wt % or equal to or greater than about 2 wt % homofarnesol based on the dry content of the crude (−)-Ambrox.

For example, the crude (−)-Ambrox may comprise equal to or less than about 5 wt % homofarnesol based on the dry content of the crude (−)-Ambrox. For example, the crude (−)-Ambrox may comprise equal to or less than about 4 wt % or equal to or less than about 3 wt % homofarnesol based on the dry content of the crude (−)-Ambrox.

For example, the crude (−)-Ambrox may comprise from about 0.05 wt % to about 5 wt % or from about 0.1 wt % to about 4 wt % or from about 0.5 wt % to about 2 wt % homofarnesol based on the dry content of the crude (−)-Ambrox.

The bioconversion methods described herein may produce (−)-Ambrox of formula (I) together with one or more by-products such as the compounds of formula (II), (III) and (IV) shown below,

TABLE 2

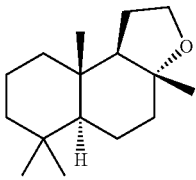 [SMILES: CC1(C)CCC[C@]2(C)[C@H]3CCO[C@]3(C)CC[C@@H]12]

Nomenclature for the compounds of formulae (I), (II), (III) and (IV)

| Compound | Description | Name and Structure |
|---|---|---|
| (I) | (−)-Ambrox | (3aR,5aS,9aS,9bR)-3a,6,6,9a-tetramethyldodecahydronaphtho[2,1-b]furan |
| (II) | Macrocycle | (7aS,11aS,Z)-5,8,8,11a-tetramethyl-2,3,6,7,7a,8,9,10,11,11a-decahydrobenzo[b]oxonine |
| (III) | 9b-epi-Ambrox | (3aR,5aS,9aS,9bS)-3a,6,6,9a-tetramethyldodecahydronaphtho[2,1-b]furan |
| (IV) | Escher et al (1990) | (3aS,5aS,9aS,9bS)-3a,6,6,9a-tetramethyldodecahydronaphtho[2,1-b]furan |

Therefore, crude (−)-Ambrox may comprise one or more compounds of formula (II), (III) and/or (IV).

For example, crude (−)-Ambrox may comprise equal to or greater than about 1 wt % total compounds of formula (II), (III) and/or (IV) based on the dry content of crude (−)-Ambrox. For example, crude (−)-Ambrox may comprise equal to or greater than about 2 wt % or equal to or greater than about 3 wt % or equal to or greater than about 4 wt % or equal to or greater than about 5 wt % or equal to or greater than about 6 wt % or equal to or greater than about 7 wt % or equal to or greater than about 8 wt % total compounds of formula (II), (III) and/or (IV) based on the dry content of crude (−)-Ambrox.

For example, crude (−)-Ambrox may comprise equal to or less than about 15 wt % total compounds of formula (II), (III) and/or (IV) based on the dry content of crude (−)-Ambrox. For example, crude (−)-Ambrox may comprise equal to or less than about 14 wt % or equal to or less than about 13 wt % or equal to or less than about 12 wt % or equal to or less than about 11 wt % or equal to or less than about 10 wt % total compounds of formula (II), (III) and/or (IV) based on the dry content of crude (−)-Ambrox.

For example, crude (−)-Ambrox may comprise from about 1 wt % to about 15 wt % or from about 3 wt % to about 12 wt % or from about 5 wt % to about 10 wt % total compounds of formula (II), (III) and/or (IV) based on the dry content of crude (−)-Ambrox.

On average, the crude (−)-Ambrox may, for example, comprise about 73.5 wt % (−)-Ambrox, 2.5 wt % (co- and by-products—the sum of compounds (II), (III) and (IV) and homofarnesol starting material), 3 wt % extraneous alcohol insoluble materials (not detected by GC analysis) and 21 wt % water.

Crude (−)-Ambrox typically contains 1.5-2.0 wt % of co- and by-product (III) (9 epi-ambrox) and 0.25-0.5% of each of co- and by-products (II) and (IV).

Crude (−)-Ambra-Oxide Starting Material

As used herein, the term "(−)-Ambra-oxide" refers to a compound of formula (X) below. (−)-Ambra-oxide may, for example, be made in combination with one or more by-products of formula (XI), (XII) or (XIII) below.

| Compound | Name and Structure |
|---|---|
| (X) | 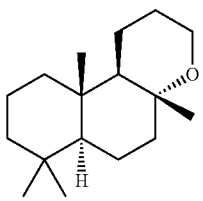 [SMILES: CC1(C)CCC[C@]2(C)[C@H]3CCCO[C@]3(C)CC[C@@H]12]<br>(4aR,6aS,10aS,10bR)-4a,7,7,10a-tetramethyldodecahydro-1H-benzo[f]chromene] ((−)-Ambra-oxide) |
| (XI) | 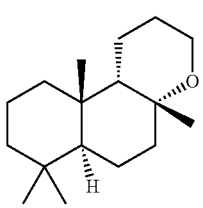 [SMILES: CC1(C)CCC[C@@]2(C)[C@H]1CC[C@@]1(C)OCCC[C@@H]21]<br>[(4aR,6aS,10aS,10bS)-4a,7,7,10a-tetramethyldodecahydro-1H-benzo[f]chromene] |
| (XII) | 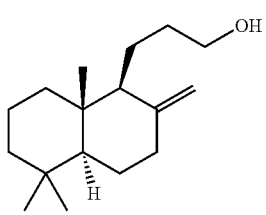 [SMILES: C=C1CC[C@H]2C(C)(C)CCC[C@]2(C)[C@H]1CCCO]<br>[3-((1S,4aS,8aS)-5,5,8a-trimethyl-2-methylenedecahydronaphthalen-1-yl)propan-1-ol] |
| (XIII) | 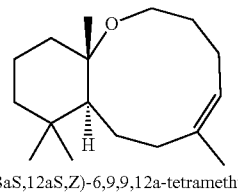<br>[(8aS,12aS,Z)-6,9,9,12a-tetramethyl-3,4,7,8,8a,9,10,11,12,12a-decahydro-2H-benzo[b]oxecine] |

(−)-Ambra-oxide can be produced from (+)-Larixol as described in Bolster et al., Tetrahedron, 2002, 58(26), pages 5275-5285.

(−)-Ambra-oxide can also be produced by enzymatically converting E,E-bishomofarnesol (BisEEH) or a mixture of isomers of bishomofarnesol comprising BisEEH to (−)-Ambra-oxide or a mixture comprising (−)-Ambra-oxide using a SHC/HAC enzyme (which may be a wild-type SHC/HAC enzyme or a variant of a wild-type SHC/HAC enzyme).

By "crude (−)-Ambra-oxide" it is meant a material comprising (−)-Ambra-oxide and impurities. As used herein, the term "impurities" refers to any solid or liquid materials that are not (−)-Ambra-oxide. This includes, for example, unreacted starting materials for the production of the (−)-Ambra-oxide (e.g. bishomofarnesol), by-products of the reaction that produces the (−)-Ambra-oxide (e.g. compounds of formula (XI), (XII) and/or (XIII)), particulate materials, cells, cell debris, and various impurities that are insoluble in solvents such as water, water-miscible solvents and organic solvents, for example impurities that are insoluble in ethanol such as precipitated mineral salts and proteins.

Therefore, by "purifying (−)-Ambra-oxide", it is meant a method that removes and reduces the amount of impurities in the crude (−)-Ambra-oxide.

The crude (−)-Ambra-oxide may have been prepared by a bioconversion process using a squalene hopene cyclase/Homofarnesol Ambrox Cyclase (SHC/HAC) enzyme (which includes wild-type enzymes and variants of wild-type enzymes) to convert E,E-bishomofarnesol to (−)-Ambra-oxide. The bioconversion broth resulting from a bioconversion process, for example as described herein, may generally comprise a solid phase containing (−)-Ambra-oxide and a liquid phase or phases containing water and/or an oily phase that may contain residual unreacted starting materials and other oily or oil-soluble impurities or by-products. The bioconversion process for the preparation of crude (−)-Ambra-oxide may, for example, be performed using the same methods described above in relation to (−)-Ambrox.

The term "crude (−)-Ambra-oxide" may refer to the material that is separated from the bioconversion broth in a pre-purification step (e.g. by filtration) prior to the purification method described herein. The separation may, for example, be performed using the same methods described in relation to (−)-Ambrox.

Crude 3a-ethyl-6,6,9a-trimethyldodecahydronaphtho[2,1-b]furan Starting Material 3a-ethyl-6,6,9a-trimethyldodecahydronaphtho[2,1-b]furan (the ethyl analogue of Ambrox having a melting point of approximately 61° C., which is approximately 10° C. lower than that of Ambrox) has the relative configuration of the structure shown in formula (XX) below, Formula (XX)

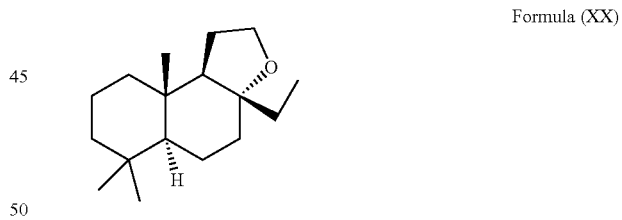

The compound of formula (XX) contains a number of chiral carbon atoms and thus one or more stereoisomers of the compound of formula (XX) may also exist, including enantiomers and diastereomers. The compound of formula (XX) may, for example, be made in combination with one or more of the stereoisomers of the compound of formula (XX).

3a-ethyl-6,6,9a-trimethyldodecahydronaphtho[2,1-b]furan can be produced by enzymatically converting ethyl-homofarnesol of formula (XXII) below or a mixture of isomers of ethylhomofarnesol to 3a-ethyl-6,6,9a-trimethyldodecahydronaphtho[2,1-b]furan or a mixture comprising 3a-ethyl-6,6,9a-trimethyldodecahydronaphtho[2,1-b]furan using a SHC/HAC enzyme (which may be a wild-type SHC/HAC enzyme or a variant of a wild-type SHC/HAC enzyme), Formula (XXII)

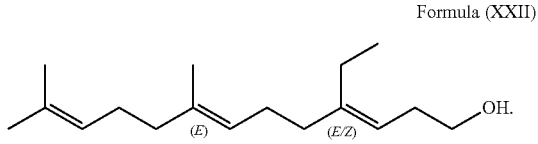 [SMILES: CC/C(=C\CCO)CC/C=C(\C)CCC=C(C)C]

By "crude 3a-ethyl-6,6,9a-trimethyldodecahydronaphtho[2,1-b]furan" it is meant a material comprising 3a-ethyl-6,6,9a-trimethyldodecahydronaphtho[2,1-b]furan and impurities. As used herein, the term "impurities" refers to any solid or liquid materials that are not 3a-ethyl-6,6,9a-trimethyldodecahydronaphtho[2,1-b]furan. This includes, for example, unreacted starting materials for the production of the 3a-ethyl-6,6,9a-trimethyldodecahydronaphtho[2,1-b]furan (e.g. ethylhomofarnesol), by-products of the reaction that produces the 3a-ethyl-6,6,9a-trimethyldodecahydronaphtho[2,1-b]furan (e.g. compounds of formula (XXI)), particulate materials, cells, cell debris, and various impurities that are insoluble in solvents such as water, water-miscible solvents and organic solvents, for example impurities that are insoluble in ethanol such as precipitated mineral salts and proteins.

Therefore, by "purifying 3a-ethyl-8,6,9a-trimethyldodecahydronaphtho[2,1-b]furan", it is meant a method that removes and reduces the amount of impurities in the crude 3a-ethyl-6,6,9a-trimethyldodecahydronaphtho[2,1-b]furan.

The crude 3a-ethyl-6,6,9a-trimethyldodecahydronaphtho[2,1-b]furan may have been prepared by a bioconversion process using a squalene hopene cyclase/Homofarnesol Ambrox Cyclase (SHC/HAC) enzyme (which includes wild-type enzymes and variants of wild-type enzymes) to convert ethylhomofarnesol to 3a-ethyl-6,6,9a-trimethyldodecahydronaphtho[2,1-b]furan. The bioconversion broth resulting from a bioconversion process, for example as described herein, may generally comprise a solid phase containing 3a-ethyl-6,6,9a-trimethyldodecahydronaphtho[2,1-b]furan and a liquid phase or phases containing water and/or an oily phase that may contain residual unreacted starting materials and other oily or oil-soluble impurities or by-products. The bioconversion process for the preparation of crude 3a-ethyl-6,6,9a-trimethyldodecahydronaphtho[2,1-b]furan may, for example, be performed using the same methods described above in relation to (−)-Ambrox.

The term "crude 3a-ethyl-6,6,9a-trimethyldodecahydronaphtho[2,1-b]furan" may refer to the material that is separated from the bioconversion broth in a pre-purification step (e.g. by filtration) prior to the purification method described herein. The separation may, for example, be performed using the same methods described in relation to (−)-Ambrox.

Crude (+)-Amberketal Starting Material (+)-Amberketal has the relative configuration of the structure shown in formula (XXX) below wherein R is methyl.

Formula (XXX)

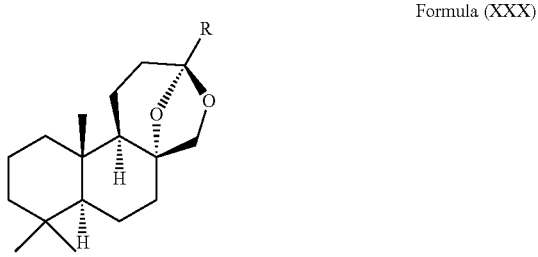

The compound of formula (XXX) contains a number of chiral carbon atoms and thus one or more stereoisomers of the compound of formula (XXX) may also exist, including enantiomers and diastereomers. The compound of formula (XXX) may, for example, be made in combination with one or more of the stereoisomers of the compound of formula (XXX).

(+)-Amberketal can be produced by enzymatically converting hydroxyfarnesylacetone of formula (XXXI) below or a mixture of isomers of hydroxyfarnesylacetone to (+)-Amberketal or a mixture comprising (+)-Amberketal using a SHC/HAC enzyme (which may be a wild-type SHC/HAC enzyme or a variant of a wild-type SHC/HAC enzyme), Formula (XXXI)

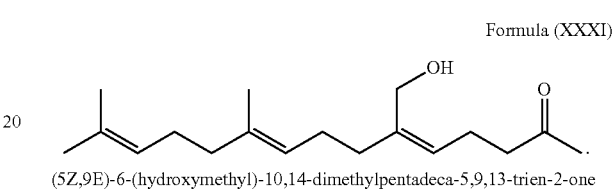

(5Z,9E)-6-(hydroxymethyl)-10,14-dimethylpentadeca-5,9,13-trien-2-one

The compound of Formula XXX may also be produced by a method comprising contacting a compound of formula (XXXIa) with a squalene-hopene cyclase (SHC) enzyme or enzyme variant, Formula (XXXIa)

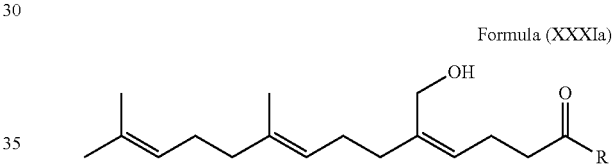

wherein R is H, methyl, or ethyl.

By "crude (+)-Amberketal" It is meant a material comprising (+)-Amberketal and impurities. As used herein, the term "impurities" refers to any solid or liquid materials that are (+)-Amberketal. This includes, for example, unreacted starting materials for the production of the (+)-Amberketal (e.g. hydroxyfarnesylacetone), by-products of the reaction that produces the (+)-Amberketal, particulate materials, cells, cell debris, and various impurities that are insoluble in solvents such as water, water-miscible solvents and organic solvents, for example impurities that are insoluble in ethanol such as precipitated mineral salts and proteins.

Therefore, by "purifying (+)-Amberketal", it is meant a method that removes and reduces the amount of impurities in the crude (+)-Amberketal The crude (+)-Amberketal may have been prepared by a bioconversion process using a squalene hopene cyclase/Homofarnesol Ambrox Cyclase (SHC/HAC) enzyme (which includes wild-type enzymes and variants of wild-type enzymes) to convert hydroxyfarnesylacetone to (+)-Amberketal. The bioconversion broth resulting from a bioconversion process, for example as described herein, may generally comprise a solid phase containing (+)-Amberketal and a liquid phase or phases containing water and/or an oily phase that may contain residual unreacted starting materials and other oily or oil-soluble impurities or by-products. The bioconversion process for the preparation of crude (+)-Amberketal may, for example, be performed using the same methods described above in relation to (−)-Ambrox.

The term "crude (+)-Amberketal" may refer to the material that is separated from the bioconversion broth in a pre-purification step (e.g. by filtration) prior to the purification method described herein. The separation may, for example, be performed using the same methods described in relation to (−)-Ambrox.

Washing

The method provided herein comprises multiple washing steps.

By "washing", it is meant that the solid material comprising the flavor or perfumery or cosmetic ingredient or intermediate, for example the solid material comprising (−)-Ambrox, is contacted with a liquid to remove one or more impurities. For example, in step (a), the liquid may be an aqueous acid. For example, in step (b), the liquid may be an aqueous alkali. For example, in step (c), the liquid may be an aqueous surfactant.

Contacting the solid material with the liquid may dissolve one or more impurities in the liquid allowing them to be separated from the solid material comprising the flavor or perfumery or cosmetic ingredient or intermediate, for example the solid material comprising (−)-Ambrox. In particular, contacting the solid material with aqueous acid may dissolve one or more impurities in the aqueous acid allowing them to be separated from the solid material comprising (−)-Ambrox.

Contacting the solid material with the aqueous surfactant may cause one or more impurities to become suspended in the liquid allowing them to be separated from the solid material comprising the flavor or perfumery or cosmetic ingredient or intermediate, for example the solid material comprising (−)-Ambrox.

Contacting the solid material with the aqueous alkali may, for example, neutralize any residual acid present from the aqueous acid washing step.

The washing may take place by dispensing the liquid over the surface of the solid material comprising the flavor or perfumery or cosmetic ingredient or intermediate, for example the solid material comprising (−)-Ambrox. The liquid may then be allowed to pass through the solid material comprising the flavor or perfumery or cosmetic ingredient or intermediate, for example the solid material comprising (−)-Ambrox, and be removed, for example naturally or using pressure or vacuum.

The washing may, for example, comprise mixing the liquid with the solid material comprising the flavor or perfumery or cosmetic ingredient or intermediate, for example the solid material comprising (−)-Ambrox. This may assist in maximizing the contact between the solid material comprising the flavor or perfumery or cosmetic ingredient or intermediate, for example the solid material comprising (−)-Ambrox, and the liquid. The liquid may then be separated from the solid comprising the flavor or perfumery or cosmetic ingredient or intermediate, for example the solid material comprising (−)-Ambrox, by filtration.

In particular, any filter cake resulting from each washing step may be re-suspended in the subsequent washing step to improve the efficiency of the subsequent washing step.

All washing steps may, for example, take place in a single piece of equipment.

The methods described herein may, for example, further comprise drying the purified flavor or perfumery or cosmetic ingredient or intermediate after the washing steps, for example further comprise drying the purified (−)-Ambrox after the washing steps. The drying step may, for example, take place in the same piece of equipment as the washing steps.

The washing and/or drying may, for example, take place in a Nutsche-type agitating and drying filter. This is a piece of equipment that can perform both filtering and drying functions and comprises an agitator (e.g. a blade) that acts to stir the material inside the vessel. The agitator may perform a number of operations through movement in axes parallel and/or perpendicular to the shaft. For example, the agitator may keep slurry contents fluidized until most mother liquor is filtered through, may help to maintain a uniform cake without cracks, may help to re-slurry a filter cake, and/or help move the filter cake towards the discharge port. A typical unit consists of a dished vessel with a perforated plate. The entire vessel can be kept at the desired temperature using a limpet jacket, jacketed bottom dish and stirrer (blade and shaft) through which heat transfer media can flow. The vessel can be made completely leak-proof for vacuum or pressure service. The drying function of the Nutsche-type agitating and drying filter may take place by applying a vacuum. This drains out the waste liquor so that the cake is ready for any subsequent washing steps.

The use of a Nutsche-type agitating and drying filter may provide advantages compared to other filters such as belt filters. In particular, the use of a Nutsche-type agitating and drying filters may improve the washing and resuspension of the solid material. For example, the use of a Nutsche-type agitating and drying fitter may reduce the amount of residual water and/or other liquid material (and impurities present in the residual water and/or other liquid material) in the product after washing compared to other types of filter (e.g. belt filters).

Each washing step (e.g. the washing with aqueous acid, the optional washing with aqueous alkali, the washing with aqueous surfactant, and/or any optional water washing steps) may use a weight ratio of washing liquid (e.g. aqueous acid, aqueous akali, aqueous surfactant, water) to dry crude material (e.g. dry crude (−)-Ambrox) of at least about 1:1. For example, each washing step may use a weight ratio of washing liquid to dry crude material (e.g. dry crude (−)-Ambrox) of at least about 2:1 or at least about 3:1. The dry crude material (e.g. dry crude (−)-Ambrox) may be the product of any previous washing steps already performed.

Each washing step (e.g. the washing with aqueous acid, the optional washing with aqueous alkali, the washing with aqueous surfactant, and/or any optional water washing steps) may use a weight ratio of washing liquid (e.g. aqueous acid, aqueous alkali, aqueous surfactant, water) to dry crude material (e.g. dry crude (−)-Ambrox) equal to or less than about 10-1. For example, each washing step may use a weight ratio of washing liquid to dry crude material (e.g. dry crude (−)-Ambrox) equal to or less than about 8:1 or at least about 6:1 or equal to or less than about 5:1. The dry crude material (e.g. dry crude (−)-Ambrox) may be the product of any previous washing steps already performed.

For example, each washing step (e.g. the washing with aqueous acid, the optional washing with aqueous alkali, the washing with aqueous surfactant, and/or any optional water washing steps) may use a weight ratio of washing liquid (e.g. aqueous acid, aqueous alkali, aqueous surfactant, water) to dry crude material, e.g. dry crude (−)-Ambrox, ranging from about 1:1 to about 10:1 or from about 2:1 to about 6:1 or from about 3:1 to about 5:1. The dry crude material (e.g. dry crude (−)-Ambrox) may be the product of any previous washing steps already performed.

The temperature of the washing liquid used for each washing step may, for example, be equal to or greater than about 5° C. The temperature of the washing liquid used for each washing step may, for example, be above room temperature (i.e. above about 22° C.). For example, the temperature of the aqueous surfactant may be above room temperature. This may, for example, assist in improving the efficiency of the washing step. For example, the temperature of the washing liquid used for each washing step may be equal to or greater than about 30° C. or equal to or greater than about 35° C. or equal to or greater than about 40° C. The temperature of the washing liquid of each washing step may, for example, be less than the melting point of the flavor or perfumery or cosmetic ingredient or intermediate, for example the (−)-Ambrox (around 72° C.-75° C.). For example, the temperature of the washing liquid of each washing step may be equal to or less than about 75° C. or equal to or less than about 70° C. or equal to or less than about 65° C. or equal to or less than about 60° C.

Aqueous Acid Washing

The acid may, for example, be any suitable acid. In particular, the acid may be any acid suitable to dissolve one or more impurities and thus enable the impurities to be separated from the solid flavor or perfumery or cosmetic ingredient or intermediate, for example the solid (−)-Ambrox. For example, the acid may be a weak or strong acid. Examples of strong acids include but are not limited to sulphuric acid or nitric acid at 0.5 to 1.0 wt %.

The acid may, for example, be a mineral acid, a sulfonic acid, a carboxylic acid or a halogenated carboxylic acid. The acid may, for example, be a compound containing an acidic phenol group.

In particular, the acid may, for example, be a weak acid. A weak acid is an acid which only partially dissociates in aqueous solution, as opposed to a strong acid which completely dissociates in aqueous solution.

Strong and weak acids may be identified by determining $pK_a$ value. The $pK_a$ value of an acid (HA) which dissociates into ions ($A^-$ and $H^+$) in aqueous solution may be determined using the following equations.

$$pK_a=-\log_{10}K_a$$

$$K_a=[A-][H+]/[HA]$$

Acids having a $pK_a$ value of less than 0 in aqueous solution are considered to be strong acids. Acids having a $pK_a$ value of 0 or more in aqueous solution are considered to be weak acids.

Examples of weak acids include, for example, oxalic acid ($HO_2C_2O_2H$), sulfurous acid ($H_2SO_3$), phosphoric acid ($H_3PO_4$), nitrous acid ($HNO_2$), boric acid ($H_3BO_3$), benzoic acid ($C_6H_5COOH$), acetic acid ($CH_3COOH$), propionic acid ($CH_3CH_3COOH$), monochloroacetic acid ($ClCH_2COOH$), dichloroacetic acid ($C_2CHCOOH$), trichloroacetic acid ($CCl_3CO_2H$), monobromoacetic acid ($BrCH_2COOH$), dibromoacetic acid ($Br_2CHCOOH$), difluoroacetic acid ($F_2CHCOOH$), trifluoroacetic acid ($F_3CCOOH$), formic acid (HCOOH), lactic acid ($CH_3CH(OH)COOH$), succinic acid (($CH_2)_2(CO_2H)_2$), uric acid ($C_5H_4N_4O_3$), malic acid ($C_4H_6O_5$), maleic acid ($HO_2CCHCHCO_2H$), tartaric acid (HOOC—CHOH—CHOH—COOH), gluconic acid ($HOCH_2$—$(CHOH)_4$—COOH), and citric acid ($C_5H_6O_7$).

The acid may, for example, be an organic acid. The acid may, for example, be a carboxylic acid.

Examples of organic and carboxylic acids include oxalic acid ($HO_2C_2O_2H$), benzoic acid ($C_6H_5COOH$), acetic acid ($CH_3COOH$), propionic acid ($CH_3CH_3COOH$), haloacetic acids (e.g. monochloroacetic acid ($ClCH_2COOH$), dichloroacetic acid ($Cl_2CHCOOH$), trichloroacetic acid ($CCl_3CO_2H$), monobromoacetic acid ($BrCH_2COOH$), dibromoacetic acid ($Br_2CHCOOH$), difluoroacetic acid ($C_2H_2F_2O_2$), trifluoroacetic acid ($C_2HF_3O_2$)), formic acid (HCOOH), lactic acid ($CH_3CH(OH)COOH$), succinic acid (($CH_2(CO_2H)_2$), uric acid ($C_5H_4NO_3$), malic acid ($C_4H_6O_5$), maleic acid ($HO_2CCHCHCO_2H$), tartaric acid (HOOC—CHOH—CHOH—COOH), gluconic acid ($HOCH_2$—$(CHOH)_4$—COOH), and citric acid ($C_6H_8O_7$).

The acid may, for example, be a weak organic acid. The acid may, for example, be a weak carboxylic acid. The acid may, for example, be an organic carboxylic acid. The acid may, for example be a weak, organic, carboxylic acid.

In certain embodiments, the add is citric acid.

The aqueous acid may, for example, have a concentration equal to or greater than about 0.01 wt %. For example, the aqueous acid may have a concentration equal to or greater than about 0.1 wt % or equal to or greater than about 0.5 wt % or equal to or greater than about 1.0 wt % or equal to or greater than about 1.5 wt % or equal to or greater than about 2.0 wt % or equal to or greater than about 2.5 wt %.

The aqueous acid may, for example, have a concentration equal to or less than about 15.0 wt %. For example, the aqueous acid may have a concentration equal to or less than about 12.5 wt % or equal to or less than about 10.0 wt % or equal to or less than about 7.5 wt % or equal to or less than about 5.0 wt % or equal to or less than about 4.0 wt % or equal to or less than about 3.0 wt %.

For example, the aqueous acid may have a concentration ranging from about 0.01 wt % to about 15.0 wt % or from about 0.5 wt % to about 10.0 wt % or from about 1.0 wt % to about 7.5 wt % or from about 2.0 wt % to about 3.0 wt %.

The aqueous acid may, for example, have a concentration equal to or greater than about 0.01 wt %. For example, the aqueous acid may have a concentration equal to or greater than about 0.1 wt % or equal to or greater than about 0.5 wt % or equal to or greater than about 1.0 wt % or equal to or greater than about 1.5 wt % or equal to or greater than about 2.0 wt % or equal to or greater than about 2.5 wt %. The aqueous acid may, for example, have a concentration equal to or less than about 5.0 wt %. For example, the aqueous acid may have a concentration equal to or less than about 4.5 wt % or equal to or less than about 4.0 wt % or equal to or less than about 3.5 wt % or equal to or less than about 3.0 wt %. For example, the aqueous acid may have a concentration ranging from about 0.01 wt % to about 5.0 wt % or from about 0.5 wt % to about 4.0 wt % or from about 1.0 wt % to about 3.0 wt % or from about 2.0 wt % to about 3.0 wt %.

The temperature of the aqueous acid may, for example, be equal to or greater than about 5° C. For example, the temperature of the aqueous acid may be equal to or greater than about 10° C. or equal to or greater than about 15° C. or equal to or greater than about 17° C.

The temperature of the aqueous acid may, for example, be equal to or less than about 50° C. For example, the temperature of the aqueous acid may be equal to or less than about 45° C. or equal to or less than about 40° C. or equal to or less than about 35° C. or equal to or less than about 30° C. or equal to or less than about 25° C. or equal to or less than about 23° C. or equal to or less than about 22° C. or equal to or less than about 21° C.

For example, the temperature of the aqueous acid may range from about 17° C. to about 50° C. or from about 17° C. to about 40° C. or from about 17° C. to about 30° C. or from about 17° C. to about 25° C. or from about 18° C. to about 22° C. or from about 20° C. to about 22° C.

The temperature of the aqueous acid may, for example, be equal to or greater than about 17° C. For example, the temperature of the aqueous acid may be equal to or greater than about 18° C. or equal to or greater than about 19° C. or equal to or greater than about 20° C. The temperature of the aqueous acid may, for example, be equal to or less than about 23° C. For example, the temperature of the aqueous acid may be equal to or less than about 22° C. or equal to or less than about 21° C. For example, the temperature of the aqueous acid may range from about 17° C. to about 23° C. or from about 18° C. to about 22° C. or from about 20° C. to about 22° C.

The washing with an aqueous acid may, for example, be repeated one or more times prior to the next step (e.g. washing with an aqueous alkali). In other words, the washing with an aqueous alkali may be carried out two or more times prior to carrying out the next step (e.g. washing with an aqueous alkali).

Where the washing with aqueous acid is repeated, there may be no other intermediate steps between the two or more washes with aqueous acid.

Where the washing with aqueous acid is repeated, at least about 90 wt %, for example at least about 95 wt % or at least about 98 wt % or at least about 99 wt % or 100 wt % of the aqueous acid from the preceding (e.g. first) wash with aqueous acid may be separated (e.g. by filtration) from the solid material comprising flavor or perfumery or cosmetic ingredient or intermediate, for example the solid material comprising (−)-Ambrox, prior to starting the next (e.g. second) wash with aqueous acid.

Aqueous Alkali Washing

The alkali may, for example, be any suitable alkali. In particular, the alkali may be any alkali suitable to neutralize any residual acid from the acid washing step. For example, the alkali may be a weak or strong alkali.

In particular, the alkali may, for example, be a strong alkali. A strong alkali is an alkali which completely dissociates in aqueous solution, as opposed to a weak alkali which only partially dissociates in aqueous solution.

Strong and weak alkalis may be identified by determining $pK_b$ value. The $pK_b$ value of an alkali (e.g. BOH) which dissociates into ions (e.g. OH⁻ and B⁺) in aqueous solution may be determined using the following equations.

$$pK_b = -\log_{10} K_b$$

$$K_b = [B^+][OH^-]/[BOH]$$

Alkalis having a $pK_b$ value of less than 0 in aqueous solution are considered to be strong alkalis. Alkalis having a $pK_b$ value of 0 or more in aqueous solution are considered to be weak alkalis.

The alkali may, for example, be a hydroxide (i.e. release a hydroxide ion when it dissociates in aqueous solution) or a carbonate or a hydrogen carbonate (bicarbonate).

Examples of alkalis include, for example, lithium hydroxide (LiOH), sodium hydroxide (NaOH), potassium hydroxide (KOH), calcium hydroxide (Ca(OH)$_2$), lithium carbonate (Li$_2$CO$_3$), sodium carbonate (Na$_2$CO$_3$), potassium carbonate (K$_2$CO$_3$), calcium carbonate (CaCO$_3$), lithium bicarbonate (LiHCO$_3$), sodium bicarbonate (NaHCO$_3$), potassium bicarbonate (KHCO$_3$) and calcium bicarbonate (Ca(HCO$_3$)$_2$).

In certain embodiments, the alkali is sodium hydroxide. The aqueous alkali may, for example, have a concentration equal to or greater than about 0.01 wt %. For example, the aqueous alkali may have a concentration equal to or greater than about 0.1 wt % or equal to or greater than about 0.5 wt % or equal to or greater than about 1.0 wt % or equal to or greater than about 1.5 wt % or equal to or greater than about 2.0 wt % or equal to or greater than about 2.5 wt %.

The aqueous alkali may, for example, have a concentration equal to or less than about 15.0 wt %. For example, the aqueous alkali may have a concentration equal to or less than about 12.5 wt % or equal to or less than about 10.0 wt % or equal to or less than about 7.5 wt % or equal to or less than about 5.0 wt % or equal to or less than about 4.0 wt % or equal to or less than about 3.0 wt %.

For example, the aqueous alkali may have a concentration ranging from about 0.01 wt % to about 15.0 wt % or from about 0.5 wt % to about 10.0 wt % or from about 1.0 wt % to about 7.5 wt % or from about 2.0 wt % to about 3.0 wt %.

The aqueous alkali may, for example, have a concentration equal to or greater than about 0.01 wt %. For example, the aqueous alkali may have a concentration equal to or greater than about 0.1 wt % or equal to or greater than about 0.5 wt % or equal to or greater than about 1.0 wt % or equal to or greater than about 1.5 wt % or equal to or greater than about 2.0 wt % or equal to or greater than about 2.5 wt %. The aqueous alkali may, for example, have a concentration equal to or less than about 5.0 wt %. For example, the aqueous alkali may have a concentration equal to or less than about 4.5 wt % or equal to or less than about 4.0 wt % or equal to or less than about 3.5 wt % or equal to or less than about 3.0 wt %. For example, the aqueous alkali may have a concentration ranging from about 0.01 wt % to about 5.0 wt % or from about 0.5 wt % to about 4.0 wt % or from about 1.0 wt % to about 3.0 wt % or from about 2.0 wt % to about 3.0 wt %.

The temperature of the aqueous alkali may, for example, be equal to or greater than about 5° C. For example, the temperature of the aqueous alkali may be equal to or greater than about 10° C. or equal to or greater than about 15° C. or equal to or greater than about 20° C. or equal to or greater than about 25° C. or equal to or greater than about 30° C. or equal to or greater than about 35° C. or equal to or greater than about 36° C. or equal to or greater than about 37° C. or equal to or greater than about 38° C. or equal to or greater than about 40° C.

The temperature of the aqueous alkali may, for example, be equal to or less than about 75° C. For example, the temperature of the aqueous alkali may be equal to or less than about 70° C. or equal to or less than about 65° C. or equal to or less than about 60° C. or equal to or less than about 55° C. or equal to or less than about 50° C. or equal to or less than about 45° C. or equal to or less than about 44° C. or equal to or less than about 43° C. or equal to or less than about 42° C. or equal to or less than about 41° C.

For example, the temperature of the aqueous alkali may range from about 5° C. to about 75° C. or from about 15° C. to about 70° C. or from about 20° C. to about 60° C. or from about 25° C. to about 50° C. or from about 35° C. to about 45° C. or from about 38° C. to about 42° C.

The temperature of the aqueous alkali may, for example, be equal to or greater than about 35° C. For example, the temperature of the aqueous alkali may be equal to or greater than about 36° C. or equal to or greater than about 37° C. or equal to or greater than about 38° C. or equal to or greater than about 39° C. or equal to or greater than about 40° C. The temperature of the aqueous alkali may, for example, be equal to or less than about 45° C. For example, the temperature of the aqueous alkali may be equal to or less than about 44° C. or equal to or less than about 43° C. or equal to or less than about 42° C. or equal to or less than about 41°

C. For example, the temperature of the aqueous alkali may range from about 35° C. to about 45° C. or from about 38° C. to about 42° C.

The washing with an aqueous alkali may, for example, be repeated one or more times prior to the next step (e.g. washing with an aqueous surfactant). In other words, the washing with aqueous alkali may be carried out two or more times prior to carrying out the next step (e.g. washing with an aqueous surfactant).

Where the washing with aqueous alkali is repeated, there may be no other intermediate steps between the two or more washes with aqueous alkali.

Where the washing with aqueous alkali is repeated, at least about 90 wt %, for example at least about 95 wt % or at least about 98 wt % or at least about 99 wt % or 100 wt % of the aqueous alkali from the preceding (e.g. first) wash with aqueous alkali may be separated (e.g. by filtration) from the solid material comprising the flavor or perfumery or cosmetic ingredient or intermediate, for example the solid material comprising (−)-Ambrox, prior to starting the next (e.g. second) wash with aqueous alkali.

Aqueous Surfactant Washing

The surfactant may, for example, be any suitable surfactant. For example, the surfactant may be any surfactant suitable for separating one or more impurities from the flavor or perfumery or cosmetic ingredient or intermediate, for example from the (−)-Ambrox. For example, the surfactant may be an anionic surfactant, a cationic surfactant, a zwitterionic surfactant or a non-ionic surfactant.

In particular, the surfactant may, for example, be an anionic surfactant. An anionic surfactant is a surfactant that contains an anionic functional group at its head. Anionic surfactants include, for example, sulfonates, phosphates, sulfates and carboxylates.

Examples of anionic surfactants include, for example, alkyl sulfates (e.g. ammonium lauryl sulfate, sodium dodecyl sulfate (SDS)), alkyl ether sulfates (e.g. sodium lauryl ether sulfate (SLES), sodium myristyl sulfate), alkyl carboxylates (e.g. stearates such as sodium stearates), alkylbenzene sulfonates, alkyl sulfonates, alkyl ether sulfonates, salts of fluorinated fatty acids, silicones, fatty alcohol sulfates, olyoxyethylene fatty alcohol ether sulfates, alpha-olefin sulfonate, polyoxyethylene fatty alcohol phosphates ether, alkyl alcohol amides, alkyl sulfonic acid acetamide, alkyl succinate sulfonate salts, amino alcohol alkylbenzene sulfonates, naphthenates, alkylphenol sulfonates, dioctyl sodium sulfosuccinate, perfluorooctanesulfonate, perfluorobutanesulfonate, alkyl-aryl ether phosphates, and alkyl ether phosphates.

In certain embodiments, the surfactant is sodium dodecyl sulfate (SDS).

Examples of non-ionic surfactants include, for example, sophorolipids, fatty alcohol ethoxylates, alkylphenol ethoxylates, fatty acid ethoxylates, ethoxylated amines and/or fatty acid amides, poloxamers, fatty acid esters of polyhydroxy compounds, fatty acid esters of glycerol, fatty acid esters of sorbitol, fatty acid esters of sucrose, alkyl polyglucosides, and amine oxides.

The aqueous surfactant may, for example, have a concentration equal to or greater than about 0.01 wt %. For example, the aqueous surfactant may have a concentration equal to or greater than about 0.05 wt % or equal to or greater than about 0.1 wt % or equal to or greater than about 0.2 wt % or equal to or greater than about 0.3 wt % or equal to or greater than about 0.4 wt % or equal to or greater than about 0.5 wt %.

The aqueous surfactant may, for example, have a concentration equal to or less than about 10.0 wt %. For example, the aqueous surfactant may have a concentration equal to or less than about 9.0 wt % or equal to or less than about 8.0 wt % or equal to or less than about 7.0 wt % or equal to or less than about 6.0 wt % or equal to or less than about 5.0 wt % or equal to or less than about 4.0 wt % or equal to or less than about 3.0 wt % or equal to or less than about 2.0 wt %

For example, the aqueous surfactant may have a concentration ranging from about 0.01 wt % to about 10.0 wt % or from about 0.05 wt % to about 8.0 wt % or from about 0.1 wt % to about 6.0 wt % or from about 0.5 wt % to about 5.0 wt % or from about 0.5 wt % to about 1.0 wt %.

The aqueous surfactant may, for example, have a concentration equal to or greater than about 0.05 wt %. For example, the aqueous surfactant may have a concentration equal to or greater than about 0.1 wt % or equal to or greater than about 0.2 wt % or equal to or greater than about 0.3 wt % or equal to or greater than about 0.4 wt % or equal to or greater than about 0.5 wt %. The aqueous surfactant may, for example, have a concentration equal to or less than about 5.0 wt %. For example, the aqueous surfactant may have a concentration equal to or less than about 4.0 wt % or equal to or less than about 3.0 wt % or equal to or less than about 2.0 wt % or equal to or less than about 1.0 wt %. For example, the aqueous surfactant may have a concentration ranging from about 0.05 wt % to about 5.0 wt % or from about 0.2 wt % to about 4.0 wt % or from about 0.3 wt % to about 3.0 wt % or from about 0.4 wt % to about 2.0 wt % or from about 0.5 wt % to about 1.0 wt %.

The temperature of the aqueous surfactant may, for example, be equal to or greater than about 5° C. For example, the temperature of the aqueous surfactant may be equal to or greater than about 10° C. or equal to or greater than about 15° C. or equal to or greater than about 20° C. or equal to or greater than about 25° C. or equal to or greater than about 30° C. or equal to or greater than about 35° C. or equal to or greater than about 40° C. or equal to or greater than about 45° C. or equal to or greater than about 50° C. or equal to or greater than about 55° C. or equal to or greater than about 60° C. or equal to or greater than about 62° C. or equal to or greater than about 64° C. or equal to or greater than about 65° C. or equal to or greater than about 66° C. or equal to or greater than about 68° C. or equal to or greater than about 70° C.

The temperature of the aqueous surfactant may, for example, be equal to or less than about 75° C. For example, the temperature of the aqueous surfactant may be equal to or less than about 74° C. or equal to or less than about 73° C. or equal to or less than about 72° C.

For example, the temperature of the aqueous surfactant may range from about 5° C. to about 75° C. or from about 35° C. to about 75° C. or from about 50° C. to about 72° C. or from about 60° C. to about 75° C.

The temperature of the aqueous surfactant may, for example, be equal to or greater than about 60° C. For example, the temperature of the aqueous surfactant may be equal to or greater than about 62° C. or equal to or greater than about 64° C. or equal to or greater than about 65° C. or equal to or greater than about 66° C. or equal to or greater than about 68° C. or equal to or greater than about 70° C. The temperature of the aqueous surfactant may, for example, be equal to or less than about 75° C. For example, the temperature of the aqueous surfactant may be equal to or less than about 74° C. or equal to or less than about 73° C. or equal to or less than about 72° C. For example, the temperature of the aqueous surfactant may range from about 60° C. to about 80° C. or from about 65° C. to about 75° C. or from about 68° C. to about 72° C.

The washing with an aqueous surfactant may, for example, be repeated one or more times. In other words, the washing with an aqueous surfactant may be carried out two or more times.

Where the washing with an aqueous surfactant is repeated, there may be no other intermediate steps between the two or more washes with aqueous surfactant.

Where the washing with an aqueous surfactant is repeated, at least about 90 wt %, for example at least about 95 wt % or at least about 98 wt % or at least about 99 wt % or 100 wt % of the aqueous surfactant from the preceding (e.g. first) wash with aqueous surfactant may be separated (e.g. by filtration) from the solid material comprising flavor or perfumery or cosmetic ingredient or intermediate, for example the solid material comprising (−)-Ambrox, prior to starting the next (e.g. second) wash with aqueous surfactant.

Additional (Optional) Steps

The methods described herein may further comprise one or more further steps before and/or after the washing with aqueous acid, the optional washing with aqueous alkali, and the washing with aqueous surfactant. For example, the methods described herein may further comprise one or more washing steps before and/or after the washing with aqueous acid, the optional washing with aqueous alkali, and the washing with aqueous surfactant.

For example, the methods described herein may further comprise washing with water between one or more of the washing with aqueous acid, the optional washing with aqueous alkali, and the washing with aqueous surfactant. For example, the methods described herein may further comprise washing with water prior to washing with aqueous acid, the optional washing with aqueous alkali, and/or the washing with aqueous surfactant. For example, the methods described herein may further comprise washing with water after any optional washing with aqueous alkali. For example, the methods described herein may further comprise washing with water after washing with aqueous acid. For example, the methods described herein may further comprise washing with water after washing with aqueous surfactant.

For example, the methods described herein may comprise washing the crude flavor or perfumery or cosmetic ingredient or intermediate with water as a first step prior to the purification method described herein.

For example, the methods described herein may comprise washing the crude (−)-Ambrox with water as a first step prior to the purification method described herein.

The temperature of the water for each additional washing step with water may, for example, be equal to or greater than about 5° C. For example, the temperature of the water for each additional washing step with water may, for example, be equal to or greater than about 10° C. or equal to or greater than about 15° C. or equal to or greater than about 20° C. or equal to or greater than about 25° C. or equal to or greater than about 30° C. or equal to or greater than about 35° C. or equal to or greater than about 40° C. or equal to or greater than about 45° C. or equal to or greater than about 50° C. or equal to or greater than about 55° C. or equal to or greater than about 60° C.

The temperature of the water for each additional washing step with water may, for example, be equal to or less than about 75° C., For example, the temperature of the water for each additional washing step with water may, for example, be equal to or less than about 74° C. or equal to or less than about 73° C. or equal to or less than about 72° C. or equal to or less than about 71° C. or equal to or less than about 70.

For example, the temperature of the water for each additional washing step with water may range from about 5° C. to about 75° C. or from about 20° C. to about 72° C. or from about 25° C. to about 70° or from about 40° C. to about 70° C. or from about 60° C. to about 70° C.

For example, the methods described herein may further comprise washing with water between the washing with aqueous alkali and the washing with aqueous surfactant. In other words, the product of the washing with aqueous alkali may be washed with water one or more times prior to washing it with an aqueous surfactant. For example, the product of the washing with aqueous alkali may be washed with water twice prior to washing it with aqueous surfactant.

The temperature of the water used to wash the product of the washing with aqueous alkali prior to washing with an aqueous surfactant may, for example be equal to or greater than about 17° C. For example, the temperature of the water may be equal to or greater than about 18° C. or equal to or greater than about 19° C. or equal to or greater than about 20° C.

The temperature of the water used to wash the product of the washing with aqueous alkali prior to washing with an aqueous surfactant may, for example, be equal to or less than about 23° C. For example, the temperature of the water may be equal to or less than about 22° C. or equal to or less than about 21° C.

For example, the temperature of the water used to wash the product of the washing with aqueous alkali prior to washing with an aqueous surfactant may range from about 17° C. to about 23° C. or from about 18° C. to about 22° C. or from about 20° C. to about 22° C.

For example, the methods described herein may further comprise washing with water after the washing with aqueous surfactant. In other words, the product of the washing with aqueous surfactant may be washed with water one or more times. For example, the product of the washing with aqueous surfactant may be washed with water two or more times, or three or more times, or four or more times. For example, the product of the washing with aqueous surfactant may be washed with water until the filtrate is clear.

For example, the product of the washing with aqueous surfactant may be washed with water one or more times, for example two times, using water having a temperature equal to or greater than about 50° C. and/or equal to or less than about 70° C., followed by washing with water one or more times, for example two times, using water having a temperature equal to or greater than about 17° C. and/or equal to or less than about 23° C. The water having a temperature equal to or greater than about 50° C. and/or equal to or less than about 70° C. may, for example, have a temperature equal to or greater than about 52° C. or equal to or greater than about 54° C. or equal to or greater than about 55° C. or equal to or greater than about 56° C. or equal to or greater than about 58° C. or equal to or greater than about 60° C. The water having a temperature equal to or greater than about 50° C. and/or equal to or less than about 70° C. may, for example, have a temperature equal to or less than about 68° C. or equal to or less than about WC or equal to or less than about 85° C. or equal to or less than about 64° C. or equal to or less than about 62° C. For example, the water having a temperature equal to or greater than about 50° C. and/or equal to or less than about 70° C. may range from about 50° C. to about 70° C. or from about 55° C. to about 65° C. or from about 58° C. to about 62° C. The water having a temperature equal to or greater than about 17° C.

and/or equal to or less than about 23° C. may, for example, have a temperature equal to or greater than about 18° C. or equal to or greater than about 19° C. or equal to or greater than about 20° C. The water having a temperature equal to or greater than about 17° and/or equal to or less than about 23° C. may, for example, have a temperature equal to or less than about 22° C. or equal to or less than about 21° C. For example, the water having a temperature equal to or greater than about 17° C. and/or equal to or less than about 23° C. may, for example, have a temperature ranging from about 17° C. to about 23° C. or from about 18° C. to about 22° C. or from about 20° C. to about 22° C.

The water used in the optional washing steps may, for example, be distilled water.

The final washing step, for example immediately prior to any drying step, may, for example, use a mixture of an alcohol and water, for example a mixture of ethanol and water, for example a 50:50 w/w mixture of ethanol and water.

After the washing steps, the product may be dried to form purified flavor or perfumery or cosmetic ingredient or intermediate. For example, the product of the washing with aqueous surfactant (and any further optional steps) may, for example, be dried to form purified flavor or perfumery or cosmetic ingredient or intermediate. For example, the product may be dried when all the washing steps have been completed.

After the washing steps, the product may be dried to form purified (−)-Ambrox. For example, the product of the washing with aqueous surfactant (and any further optional steps) may, for example, be dried to form purified (−)-Ambrox. For example, the product may be dried when all the washing steps have been completed.

Purified Flavor or Perfumery or Cosmetic Ingredient or Intermediate Product

The product of the methods described herein may be referred to as purified flavor or perfumery or cosmetic ingredient or intermediate. There is provided herein purified flavor or perfumery or cosmetic ingredient or intermediate obtained by or obtainable by the methods described herein, including all embodiments thereof.

Purified (−)-Ambrox Product

The product of the methods described herein may be referred to as purified (−)-Ambrox. There is provided herein purified (−)-Ambrox obtained by or obtainable by the methods described herein, including all embodiments thereof.

In certain embodiments, the purified (−)-Ambrox is in a solid form as described in WO 2017/182542, the contents of which are incorporated herein by reference.

The purified (−)-Ambrox may, for example, comprise equal to or greater than about 98.0 wt % (−)-Ambrox based on the dry material. For example, the purified (−)-Ambrox may comprise equal to or greater than about 98.5 wt % or equal to or greater than about 99.0 wt % (−)-Ambrox based on the dry material. The purified (−)-Ambrox may, for example, comprise equal to or less than about 99.5 wt % (−)-Ambrox based on the dry solid material. For example, the purified (−)-Ambrox may comprise from about 98.0 wt % to about 99.5 wt % or from about 98.5 wt % to about 99.5 wt % or from about 99.0 wt % to about 99.5 wt % (−)-Ambrox based on the dry solid material.

The compounds of formula (II), (III) and (IV) and unreacted homofarnesol may be present in the purified (−)-Ambrox in an olfactory acceptable amount. This means that the compounds of formula (II), (III) and (IV) are present in amounts below their odor detection thresholds, or in an amount at which it will not contribute its olfactory characteristics in a way that will affect the olfactory characteristics of (−)-Ambrox. Purified (−)-Ambrox containing an olfactory acceptable amount of any such compound would be identifiable to a skilled perfumer as possessing the odor character of commercial grades of (−)-Ambrox such as AMBROFIX™ obtained by a synthetic procedure ex-sclareol, and available from Givaudan.

The purified (−)-Ambrox may, for example, comprise equal to or greater than about 0.1 wt % or equal to or greater than about 0.2 wt % of the compound of formula (II) based on the dry material. The purified (−)-Ambrox may, for example, comprise equal to or less than about 0.4 wt % or equal to or less than about 0.3 wt % of the compound of formula (II) based on the dry material.

The purified (−)-Ambrox may, for example, comprise equal to or greater than about 0.1 wt % or equal to or greater than about 0.2 wt % of the compound of formula (III) based on the dry material. The purified (−)-Ambrox may, for example, comprise equal to or less than about 0.4 wt % or equal to or less than about 0.3 wt % of the compound of formula (III) based on the dry material.

The purified (−)-Ambrox may, for example, comprise equal to or greater than about 0.1 wt % or equal to or greater than about 0.2 wt % of the compound of formula (IV) based on the dry material. The purified (−)-Ambrox may, for example, comprise equal to or less than about 0.8 wt % or equal to or less than about 0.6 wt % or equal to or less than about 0.4 wt % of the compound of formula (IV) based on the dry solid material.

The purified (−)-Ambrox may, for example, comprise equal to or greater than about 0.3 wt % or equal to or greater than about 0.4 wt % or equal to or greater than about 0.5 wt % total compounds of formulas (II), (III) and (IV) based on the dry material. The purified (−)-Ambrox may, for example, comprise equal to or less than about 1.2 wt % or equal to or less than about 1.0 wt % or equal to or less than about 0.8 wt % total compounds of formulas (II), (III) and (IV) based on the dry material.

The purified (−)-Ambrox may, for example, comprise equal to or greater than about 0.1 wt % or equal to or greater than about 0.2 wt % or equal to or greater than about 0.3 wt % or equal to or greater than about 0.4 wt % of unreacted homofarnesol based on the dry material. The purified (−)-Ambrox may, for example, comprise equal to or less than about 0.8 wt % or equal to or less than about 0.7 wt % or equal to or less than about 0.6 wt % of the compound of unreacted homofarnesol based on the dry material.

The wt % of each compound in the purified (−)-Ambrox may be determined by gas chromatography.

The methods described herein may provide (−)-Ambrox in a yield equal to or greater than about 95 mol % based on the crude starting material. For example, the methods described herein may provide (−)-Ambrox in a yield equal to or greater than about 96 mol % or equal to or greater than about 97 mol % or equal to or greater than about 98 mol % based on the crude starting material. For example, the methods described herein may provide (−)-Ambrox in a yield equal to or less than about 100 mol % or equal to or less than about 99 mol % based on the crude starting material.

The purified (−)-Ambrox may, for example, be analyzed by X-Ray Diffraction (XRD).

Powder XRD data can be collected in a straightforward manner using diffractometer equipment well known in the art.

Powder XRD patterns may be acquired using a STOE STADI P X-ray diffractometer. System description: The diffractometer was used in transmission mode (flat sample holders, curved Germanium (111) monochromator, and CuKα1 radiation 1.54060 Angstrom) by using a position-sensitive detector. The generator Voltage was 40 kV and the current 40 mA. The detector: Mythen IK. Experimental parameters: Pattern measurement was made between 2 theta=about 4° to 26°. The accuracy of the diffraction angles determined is approximately +/−2° 2 theta.

The purified (−)-Ambrox may, for example, exhibit a powder x-ray diffraction pattern having at least one of the following peaks at diffraction angles 2 theta of about 15.6, 16.2, 16.7, 17.0, 17.4, 18.3+/−0.2°.

The solid form of the purified (−)-Ambrox may, for example, be characterized by a powder x-ray diffraction pattern exhibiting the following peaks at diffraction angles 2 theta of about 15.6, 16.2, 16.7, 17.0, 17.4 and 18.3+/−0.2°.

The solid form of the purified (−)-Ambrox may, for example, be characterized by a powder x-ray diffraction pattern substantially as depicted in FIG. 1, below.

The shape of the crystals can be determined by microscopy according to methods well known in the art.

Average diameter measurements of the crystals may be determined by laser granulometry. Laser granulometry is a technique well known in the art. Average particle size can be determined on any particle size analyser known for such purpose, for example a CILAS 1180 No. 516 instrument. Measurements can be made in accordance with the ISO standard 13320-1 (2009 revision) using the Fraunhofer method with water as carrier liquid and an Obscuration Index of 24.

The solid form of the purified (−)-Ambrox may, for example, comprise elongate crystals having an average diameter of between 10 to 400 microns, for example between 40 and 400 microns, for example between 100 about 400 microns.

The solid form of the purified (−)-Ambrox may, for example, comprise elongate crystals having a length measured along their longest dimension of 20 to 600 microns, for example 40 to 500 microns, for example 100 to 400 microns, for example greater than 100 microns, for example greater than 200 microns, for example greater than 300 microns.

The purified (−)-Ambrox comprises (−)-Ambrox as a predominant compound but may also comprise other compounds which may or may not impart pleasant olfactive notes to the bioconversion mixture and so may contribute in a positive or negative manner to the sensory character of the purified (−)-Ambrox end product. Accordingly, a sensory analysis of the purified (−)-Ambrox may be carried out using well-established sensory tests utilized by trained experts (e.g. Perfumers) so that the testing can assist in determining if the chemically relevant target product is also an olfactory relevant end product relative to a reference product.

The purified (−)-Ambrox product may be tested against a commercially available reference of (−)-Ambrox for its olfactory purity, quality and its sensory profile. The (−)-Ambrox material may also be tested in application studies by experts in order to determine if the material meets the specifications with respect to its organoleptic profile. Various applications for (−)-Ambrox include but are not limited to a fine fragrance or a consumer product such as fabric care, toiletries, beauty care and cleaning products including essentially all products where the currently available Ambrox ingredients are used commercially, including but not limited to: Ambrox (Firmenich), Ambroxan (Henkel), Ambrofix (Givaudan), Amberlyn (Quest), Cetalox Laevo (Firmenich), Ambermor (Aromor) and Norambrenolide Ether (Pacific) products.

The reference product for the purified (−)-Ambrox described herein may, for example, be a solid form of (−)-Ambrox made according to a method as described in WO 2017/182542, for example Example 4 of WO 2017/182542.

The reference product for the purified (−)-Ambrox described herein may, for example, be (−)-Ambrox flakes ex scareolide made according to a method as described in VO 2018/154048.

"Sclareolide" is used as a synonym for "(3aR, 5aS, 9aS, 9bR)-3a,6,6,9a-tetramethyl-1,4,5,5a,7,8,9,9b-octahydrobenzo[e]benzofuran-2-one". Dextrorotatory or (+)-scareolide has the following structural formula:

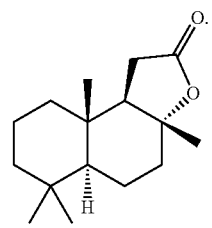 [SMILES: CC1(C)CCC[C@]2(C)[C@H]3CC(=O)O[C@]3(C)CC[C@@H]12]

Sclareolide, as for example obtained by the cycase-catalyzed conversion of (3E/7E)-homofarnesylic acid which then is chemically reduced (for example by means of LiAlH$_4$ or NaBH$_4$) to form Ambrox-1,4-diol [Mookherjee et al.; *Perfumer and Flavourist* (1990), 15:27]. Ambrox-1,4-diol may then be chemically converted by means of different processes to (−)-Ambrox (see, for example, U.S. Pat. No. 5,274,134).

The reference product for the purified (−)-Ambrox described herein may, for example, be (−)-Ambrox made by any method known to those skilled in the art.

For example, (−)-Ambrox was originally discovered after chemical transformations of clary sage (*Salvia sclarea* L.) ingredients (see M. Hinder, M. Stoll, *Hlv. Chim. Acta* 1950, 33, 1308-1312) and later identified as a key odorant of alcoholic ambergris tinctures (see B. D. Mookherjee, R. R. Patel, Proceedings 7$^{th}$ Int. Congr. Ess. Oils 1977, Kyoto. Japan, Paper No 136).

Ambrox was traditionally manufactured by different companies on a combined >100 t/a scale by semisynthesis from (+)-sclareol (9.1.1 below), a diterpene diol isolated from clary sage:

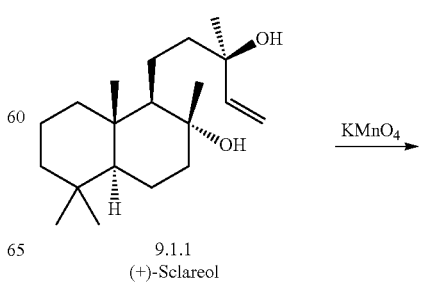

9.1.1
(+)-Sclareol

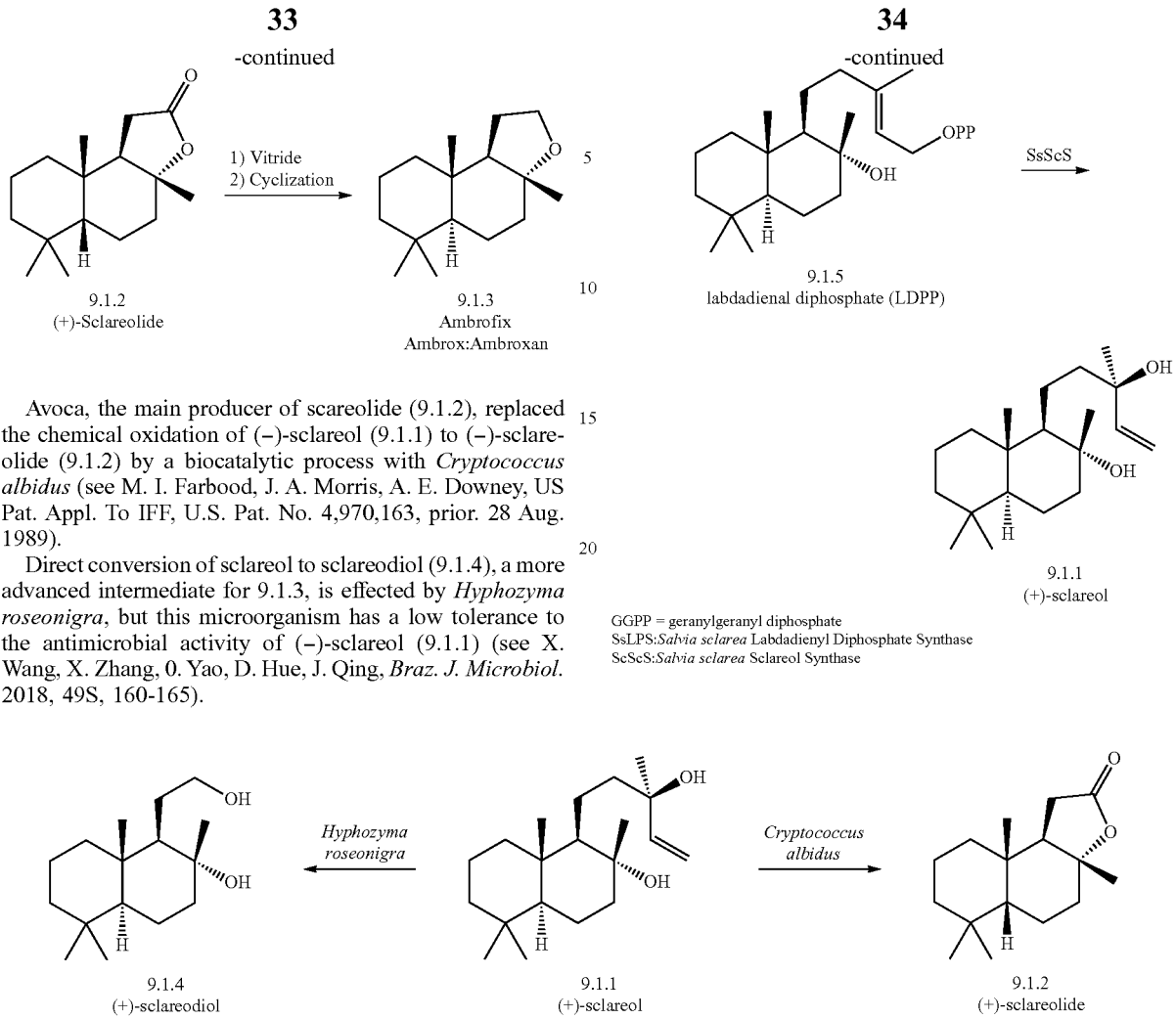

Avoca, the main producer of scareolide (9.1.2), replaced the chemical oxidation of (−)-sclareol (9.1.1) to (−)-sclareolide (9.1.2) by a biocatalytic process with *Cryptococcus albidus* (see M. I. Farbood, J. A. Morris, A. E. Downey, US Pat. Appl. To IFF, U.S. Pat. No. 4,970,163, prior. 28 Aug. 1989).

Direct conversion of sclareol to sclareodiol (9.1.4), a more advanced intermediate for 9.1.3, is effected by *Hyphozyma roseonigra*, but this microorganism has a low tolerance to the antimicrobial activity of (−)-sclareol (9.1.1) (see X. Wang, X. Zhang, 0. Yao, D. Hue, J. Qing, *Braz. J. Microbiol.* 2018, 49S, 160-165).

Aiming at production of 9.1.3 (Ambroflix/Ambrox/Ambroxan) independent from plant-sourced materials, Schalk et al. transferred the biogenetic scdareol pathway into *E. coli* (see M. Schalk, L. Pastore, M A. Mirata, S. Khim, M. Schouwey, F. Deguerry, V. Pineda, L. Rocci, L. Daviet, *J. Am. Chem. Soc.* 2012, 134, 18900-18903). The biosynthesis from geranylgeranyl diphosphate (GGPP) involved two diterpene cyclases (see scheme below). The corresponding genes were functionally expressed in an *E. coli* strain genetically modified for overproduction of GGPP, which allowed the production of (−)-sclareol (9.1.1) at 1.5 g/L Based on these results, an industrial fermentation process in yeast was developed, which led to a new quality of Ambrox named Ambrox Super (not to be confused with "Superambrox", the 5(6)-dehydro-Ambrox (see R. L Snowden, *Chem. Biodiv.* 2008, 5, 958-989).

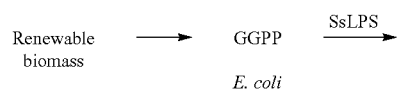

Uses of the Purified Products

There is further provided herein the use of the purified flavor ingredient described herein as a flavor ingredient. Flavor ingredients can be used in consumer food and drink product applications.

Thus, there is also provided herein a flavor composition comprising the purified flavor ingredient described herein. A "flavor composition" may, for example, be any composition comprising the purified flavor ingredient. The flavor composition may, for example, further comprise other flavor ingredients, carrier materials, diluents or combinations thereof.

There is also provided herein a food or drink product comprising a flavor composition as described herein.

There is further provided herein the use of the purified cosmetic ingredient described herein as a cosmetic ingredient. Cosmetic ingredients can be used in cosmetic products.

Thus, there is also provided herein a cosmetic composition comprising the purified cosmetic ingredient described herein. A "cosmetic composition" may, for example, be any composition comprising the purified cosmetic ingredient. The cosmetic composition may, for example, further comprise other cosmetic ingredients, carrier materials, diluents, or combinations thereof.

There is also provided herein a cosmetic product comprising a flavour ingredient or flavour composition as described herein. The cosmetic product may, for example, be a skin care product (e.g. moisturizer), make-up product (e.g. foundation, concealer, lipstick, eyeshadow, eyeliner), a haircare product (e.g. shampoo, conditioner, dye), oral hygiene products (e.g. toothpaste, mouthwash), or deodorant.

There is further provided herein the use of the purified (−)-Ambrox described herein as a flavor ingredient.

There is further provided herein the use of the purified perfumery ingredient described herein, for example purified (−)-Ambrox described herein, as a perfumery ingredient. Perfumery ingredients can be used in both consumer product applications and in fine fragrance applications.

Thus, there is also provided herein a perfume composition comprising the purified perfumery ingredient described herein, for example the purified (−)-Ambrox described herein. A "perfume composition" may, for example, be any composition comprising the purified perfumery ingredient, for example the purified (−)-Ambrox and a base material.

As used herein, the "base material" includes all known fragrance ingredients selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, and other auxiliary agents commonly used in the art.

Fragrance ingredients known to the art are readily available commercially from the major fragrance manufacturers. Non-limiting examples of such ingredients include:

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((2)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,62)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-ylbut-3-en-2-one); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo [4.1.0]heptane-2,5'-[1,3]dioxane];

macrocycles, e.g. Ambrettolide ((2)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

As used herein, "carrier material" means a material which is practically neutral from an odorant point of view, i.e. a material that does not significantly alter the organoleptic properties of odorants.

By "diluents" is meant any diluent conventionally used in conjunction with odorants, such as diethyl phthalate (DEP), dipropylene glycol (DPG), isopropyl myristate (IPM), triethyl citrate (TEC) and alcohol (e.g. ethanol).

The term "auxiliary agent" refers to ingredients that might be employed in a perfume composition for reasons not specifically related to the olfactive performance of said composition. For example, an auxiliary agent may be an ingredient that acts as an aid to processing a perfume ingredient or ingredients, or a composition containing said ingredient(s), or it may improve handling or storage of a perfume ingredient or composition containing same, such as anti-oxidant adjuvant. Said anti-oxidant may be selected, for example, from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

It might also be an ingredient that provides additional benefits such as imparting colour or texture. It might also be an ingredient that imparts light resistance or chemical stability to one or more ingredients contained in a perfume composition.

A detailed description of the nature and type of auxiliary agent commonly used in perfume compositions containing same cannot be exhaustive, but it has to be mentioned that said ingredients are well known to a person skilled in the art.

There is also provided herein a consumer product comprising a perfume composition as described herein, including any embodiment thereof. The consumer product may, for example, be a household care (e.g. cleaning), personal care (e.g. a cosmetic), laundry care, or air care composition.

The following numbered paragraphs define particular embodiments of the present invention:

1. A method for purifying a crude flavor or perfumery or cosmetic ingredient or intermediate, the method comprising:
   washing with an aqueous acid;
   washing with an aqueous surfactant; and
   optionally washing with an aqueous alkali.
2. The method of paragraph 1, wherein the crude flavor or perfumery or cosmetic ingredient or intermediate is in solid form.
3. The method of paragraph 1 or 2, wherein the crude flavor or perfumery or cosmetic ingredient or intermediate was made by a bioconversion process.

4. The method of any preceding paragraph, wherein the crude flavor or perfumery or cosmetic ingredient or intermediate was made by a bioconversion process using a SHC/HAC enzyme.
5. The method of any preceding paragraph, wherein the method is a method for purifying crude (−)-Ambrox, crude (−)-Ambra-oxide, crude 3a-ethyl-6,6,9a-trimethyldodecahydronaphtho[2,1-b]furan or crude (+)-Amberketal.
6. The method of any preceding paragraph, wherein the method comprises:
    (a) washing the crude flavor or perfumery or cosmetic ingredient or intermediate with an aqueous acid;
    (b) washing the product of step (a) with an aqueous alkali;
    (c) washing the product of step (b) with an aqueous surfactant.
7. The method of any preceding paragraph, wherein the acid is a weak acid.
8. The method of any preceding paragraph, wherein the acid is an organic acid.
9. The method of any preceding paragraph, wherein the acid is citric acid.
10. The method of any preceding paragraph, wherein the aqueous acid has a concentration equal to or greater than about 0.01 wt % and/or equal to or less than about 15.0 wt %, for example from about 0.1 wt % to about 5.0 wt %.
11. The method of any preceding paragraph, wherein the temperature of the aqueous acid ranges from about 17° C. to about 50° C., for example from about 17° C. to about 23° C.
12. The method of any preceding paragraph, wherein the washing with aqueous acid is repeated one or more times prior to the washing with aqueous alkali.
13. The method of any preceding paragraph, wherein the alkali is a strong alkali.
14. The method of any preceding paragraph, wherein the alkali is a hydroxide.
15. The method of any preceding paragraph, wherein the alkali is sodium hydroxide.
16. The method of any preceding paragraph, wherein the aqueous alkali has a concentration equal to or greater than about 0.01 wt % and/or equal to or less than about 15.0 wt %, for example from about 0.1 wt % to about 5.0 wt %.
17. The method of any preceding paragraph, wherein the temperature of the aqueous alkali ranges from about 5° C. to about 75° C., for example from about 35° C. to about 45° C.
18. The method of any preceding paragraph, wherein the washing with aqueous alkali is repeated one or more times prior to the washing with aqueous surfactant.
19. The method of any preceding paragraph, wherein the surfactant is an anionic surfactant.
20. The method of any preceding paragraph, wherein the surfactant is sodium dodecylsulfate (SDS).
21. The method of any preceding paragraph, wherein the aqueous surfactant has a concentration equal to or greater than about 0.01 wt % and/or equal to or less than about 10.0 wt %, for example from about 0.1 wt % to about 5.0 wt %.
22. The method of any preceding paragraph, wherein the temperature of the aqueous surfactant ranges from about 5° C. to about 75° C., for example from about 60° C. to about 70° C.
23. The method of any preceding paragraph, wherein the washing with aqueous surfactant is repeated one or more times.
24. The method of any preceding paragraph, further comprising one or more steps of washing with water prior to or after the washing with aqueous acid, the washing with aqueous alkali and/or the washing with aqueous surfactant.
25. The method of any preceding paragraph, wherein the product of the washing with aqueous alkali is washed with water prior to washing with an aqueous surfactant.
26. The method of paragraph 24 or 25, wherein the temperature of the water ranges from about 5° C. to about 75° C., for example from about 17° C. to about 23° C.
27. The method of paragraph 25 or 26, wherein the product of the washing with aqueous alkali is washed with water two or more times prior to washing with an aqueous surfactant.
28. The method of any preceding paragraph, wherein the product of the washing with aqueous surfactant is washed with water.
29. The method of paragraph 28, wherein the product of the washing with aqueous surfactant is washed with water having a temperature ranging from about 50° C. to about 70° C. followed by washing with water having a temperature ranging from about 17° C. to about 23° C.
30. The method of paragraph 28 or 29, wherein the product of the washing with aqueous surfactant is washed with water having a temperature ranging from about 50° C. to about 70° C. two or more times.
31. The method of any of paragraphs 28 to 31, wherein the product of the washing with aqueous surfactant is washed with water having a temperature ranging from about 17° C. to about 23° C. two or more times.
32. The method of any preceding paragraph m, wherein the crude flavor or perfumery or cosmetic ingredient or intermediate, for example the crude (−)-Ambrox, is separated from a bioconversion broth prior to the method of purification.
33. The method of paragraph 31, wherein the separation of the crude flavor or perfumery or cosmetic ingredient or intermediate, for example the crude (−)-Ambrox, takes place by physical means, for example by filtration.
34. The method of paragraph 33, wherein the bioconversion broth is subject to a heat inactivation step or an alkalinisation step prior to the separation.
35. The method of paragraph 34, wherein the alkalinisation takes place by increasing the pH of the bioconversion broth to a pH from about 10 to about 11.
36. The method of paragraph 34, wherein the heat inactivation takes place by increasing the temperature of the bioconversion broth to a maximum temperature of 55° C.
37. The method of any preceding paragraph, wherein all the washing steps take place in a single piece of equipment.
38. The method of any preceding paragraph, wherein all the washing steps take place in a Nutsche-type agitating and drying filter.
39. The method of paragraph 38, wherein the crude flavor or perfumery or cosmetic ingredient or intermediate, for example the crude (−)-Ambrox, comprises from about 20 wt % to about 30 wt % water based on the wet weight of the crude (−)-Ambrox.

40. A flavor or perfumery or cosmetic ingredient or intermediate, for example (−)-Ambrox, obtained by or obtainable by the method of any of paragraphs 1 to 39.
41. Use of the flavor or perfumery or cosmetic ingredient, for example (−)-Ambrox, of paragraph 40 as a flavor or perfumery or cosmetic ingredient.
42. A perfume composition comprising the perfumery ingredient, for example (−)-Ambrox, of paragraph 40.
43. A flavor composition comprising the flavor ingredient of paragraph 40.
44. A cosmetic composition comprising the cosmetic ingredient of paragraph 40.
45. A household care, personal care, laundry care or air care composition comprising a perfume composition of paragraph 42.
46. A food or drink product comprising a flavor composition of paragraph 43.
47. A cosmetic product comprising a cosmetic composition of paragraph 44.
48. A Nutsche-type agitating and drying filter configured to purify a crude flavor or perfumery ingredient or intermediate, for example a crude (−)-Ambrox, by the method of any one of paragraphs 1 to 39, wherein the crude flavor or perfumery ingredient or intermediate, for example the crude (−)-Ambrox comprises from about 20 wt % to about 30 wt % water based on the wet weight of the crude flavor or perfumery ingredient or intermediate, for example the crude (−)-Ambrox.
49. A process for purifying a crude flavor or perfumery ingredient or intermediate, the process comprising washing the crude flavor or perfumery ingredient or intermediate in a Nutsche-type agitating and drying filter.
50. The process of paragraph 47, wherein the process is according to any of paragraphs 1 to 39.

EXAMPLES

Example 1

Preparation of the crude (−)-Ambrox

For the avoidance of doubt, all reference to WT SHC and SHC variants are references to WT AacSHC (SEQ ID NO. 1) and variants thereof.

SEQ ID NO: 1: amino acid sequence of *Alicyclobacillus acidocaldarius* SHC (AacSHC)

```
MAEQLVEAPAYARTLDRAVEYLLSCQKDEGYWWGPLLSNVTMEAEYVLL

CHILDRVDRDRMEKIRRYLLHEQREDGTWALYPGGPPDLDTTIEAYVAL

KYIGMSRDEEPMQKALRFIQSQGGIESSRVFTRMWLALVGEYPWEKVPM

VPPEIMFLGKRMPLNIYEFGSWARATVVALSIVMSRQPVFPLPERARVP

ELYETDVPPRRRGAKGGGGWIFDALDRALHGYQKLSVHPFRRAAEIRAL

DWLLERQAGDGSWGGIQPPWFYALIALKILDMTQHPAFIKGWEGLELYG

VELDYGGWMFQASISPVWDTGLAVLALRAAGLPADHDRLVKAGEWLLDR

QITVPGDWAVKRPNLKPGGFAFQFDNVYYPDVDDTAVVVWALNTLRLPD

ERRRRDAMTKGFRWIVGMQSSNGGWGAYDVDNTSDLPNHIPFCDFGEVT

DPPSEDVTAHVLECFGSFGYDDAWKVIRRAVEYLKREQKPDGSWFGRWG

VNYLYGTGAVVSALKAVGIDTREPYIQKALDWVEQHQNPDGGWGEDCRS
```
-continued
```
YEDPAYAGKGASTPSQTAWALMALIAGGRAESEAARRGVQYLVETQRPD

GGWDEPYYTGTGFPGDFYLGYTMYRHVFPTLALGRYKQAIERR
```

The 215G2 SHC variant includes the mutations M132R, A224V and I432T compared to WT AacSHC.

Biocatalyst Production

Methods 1

SHC Plasmid Preparation

The gene encoding *Alicyclobacillus acidocaldarius* squalene hopene cyclase variant 215G2 SHC was inserted into plasmid pET-28a(+), where it is under the control of an IPTG inducible T7-promotor for protein production in *Escherichia coli*. A plasmid map for pET-28a(+) (5369 bp) is shown in FIG. 5 of WO 2016/170099. The cloning and expression regions of the pET-28a(+) plasmid are shown in FIG. 21 of WO 2016/170099. The plasmid was transformed into *E. coli* strain BL21(DE3) using a standard heat-shock transformation protocol.

Erlenmeyer Flask Cultures

For protein production were used either complex (LB) or minimal media. M9 is one example of minimal media, which were successfully used.

Media Preparation

The minimal medium chosen as default was prepared as follows for 350 ml culture: to 35 ml citric acid/phosphate stock (133 g/l $KH_2PO_4$, 40 g/l $(NH_4)_2HPO_4$, 17 g/l citric acid. $H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (composition in next section) solution, 0.035 ml Thiamine solution and 7 ml 20% glucose were added.

SHC Biocatalyst Production (Biocatalyst Production)

Small scale biocatalyst production (wild-type SHC or SHC variants), 350 ml culture (medium supplemented with 50 μg/ml kanamycin) were inoculated from a preculture of the *E. coli* strain BL21(DE3) containing the SHC production plasmid. Cells were grown to an optical density of approximately 0.5 ($OD_{650nm}$) at 37° C. with constant agitation (250 rpm).

Protein production was then induced by the addition of IPTG to a concentration of 300 μM followed by incubation for a further 5-6 hours with constant shaking. The resulting biomass was finally collected by centrifugation, washed with 50 mM Tris-HCl buffer pH 7.5. The cells were stored as pellets at 4° C. or −20° C. until further use. In general 2.5 to 4 grams of cells (wet weight) were obtained from 1 liter of culture, independently of the medium used.

Fermentations were prepared and run in 750 ml InforsHT reactors. To the fermentation vessel was added 168 ml deionized water. The reaction vessel was equipped with all required probes ($pO_2$, pH, sampling, antifoam), C+N feed and sodium hydroxide bottles and autoclaved.

After autoclaving is added to the reactor
20 ml 10× phosphate/citric acid buffer
14 ml 50% glucose
0.53 ml $MgSO_4$ solution
2 ml $(NH_4)_2SO_4$ solution
0.020 ml trace elements solution
0.400 ml thiamine solution
0.200 ml kanamycin stock The running parameters were set are as follows: pH=6.95, $pO_2$=40%, T=30° C., Stirring at 300 rpm. Cascade: rpm setpoint at 300, min 300, max 1000, flow l/min set point 0.1, min 0, max 0.6. Antifoam control: 1:9.

The fermenter was inoculated from a seed culture to an $OD_{650nm}$ of 0.4-0.5. This seed culture was grown in LB medium (+ Kanamycin) at 37° C., 220 rpm for 8 h. The fermentation was run first in batch mode for 11.5 h, where after was started the C+ N feed with a feed solution (sterilized glucose solution (143 ml $H_2O$+ 35 g glucose) to which had been added after sterilization: 17.5 ml $(NH_4)_2SO_4$ solution, 1.8 ml $MgSO_4$ solution, 0.018 ml trace elements solution, 0.360 ml Thiamine solution, 0.180 ml kanamycin stock. The feed was run at a constant flow rate of approx. 4.2 ml/h. Glucose and $NH_4^+$ measurements were done externally to evaluate availability of the C- and N-sources in the culture. Usually glucose levels stay very low.

Cultures were grown for a total of approx. 25 hours, where they reached typically and $OD_{650nm}$ of 40-45. SHC production was then started by adding IPTG to a concentration of approx. 1 mM In the fermenter (as IPTG pulse or over a period of 3-4 hours using an infusion syringe), setting the temperature to 40° C. and $pO_2$ to 20%. Induction of SHC production lasted for 16 h at 40° C. At the end of induction the cells were collected by centrifugation, washed with 0.1 M citric acid/sodium citrate buffer pH 5.4 and stored as pellets at 4° C. or −20° C. until further use.

In general, with all other conditions unchanged the specific activity of the produced biocatalyst was higher when a minimal medium was used compared with a complex medium. Induction was carried out successfully at 30 or 37° C. It was noted that when the induction was done at 40-43° C., a biocatalyst of higher specific activity was obtained. A fermentation yielded typically between 20 and 30 grams of cells (wet weight).

Biotransformation at 125 g/l E,E-Homofarnesol (EEH)

A typical EEH bioconversion reaction contained 125 g/l EEH, 250 g/l wet weight of cells that had produced 215G2 SHC, 1.3% SDS in 0.1 M succinic acid/NaOH buffer pH 5.4.

The reaction is incubated at 35° C. under constant agitation. The cell wet weight concentration of the cell suspension used for preparing the bioconversion can e.g. be determined by centrifugation of an aliquot of this cell suspension for 10 min at 10° C. and 17210 g in order to calculate the volume of cell suspension required to set the cell concentration to 250 g/l in the EEH bioconversion reaction. EEH conversion is completed within 72 hours of reaction, usually.

Purification of the Crude (−)-Ambrox

The crude (−)-Ambrox contained 70-75 wt % dry materials and 20-25 wt % water. The dry material contained 5-10 wt % chemical and insoluble impurities.

The crude (−)-Ambrox was purified by the following procedure:

1) two washes with room temperature 2.5 wt % aqueous citric acid;
2) two washes with 40° C. 0.1 wt % aqueous sodium hydroxide;
3) two washes with room temperature water;
4) two washes with 70° C. 0.5 wt % sodium dodecylsulfate (SDS);
5) two washes with 60° C. water;
6) two or three washes with room temperature water (until filtrate is clear);

Highly pure (>99% by GC analysis) olfactory grade (−)-Ambrox was obtained, with an average yield of 95 mol % based on the crude starting material (thought to be due to mechanical losses during transfers from the washing reactor to the Buchner filter and vice-versa).

Example 2

Crude (−)-Ambrox was obtained by the same process described for Example 1.

10 kg of crude (−)-Ambrox containing 77.9 wt % (−)-Ambrox, 18.2 wt % water and 3.9 wt % chemical and insoluble impurities was charged in a 50 litre capacity stainless steel Nutsche type agitated filter fitted with a two bladed bottom entry agitator and a 5 micron filtering cloth. The crude (−)-Ambrox was purified by the following procedure:

1) 2 washes with 20 kg each of ambient temperature 2.5 wt % aqueous oxalic acid,
2) 2 washes with 20 kg each of warm (40° C.) 0.1 wt % aqueous sodium hydroxide,
3) 2 rinses with 20 kg each of ambient temperature water,
4) 1 wash with 20 kg of warm (40° C.) 0.5 wt % aqueous sodium dodecylsulfate (SDS),
5) 2 rinses with 20 kg each of warm (40° C.) water,
6) 3 rinses with 20 kg each of ambient temperature water,
7) 2 final rinses with 20 kg each of ambient temperature 50 wt % aqueous ethanol.

The slurry was agitated for 30 minutes during each wash and for 15 minutes during each rinse. The agitator was then stopped and the waste aqueous liquors were completely drained out of the filter by suction before the next wash or rinse was charged.

After the final hydro-alcoholic rinses, the cake was dried in the filter, with intermittent stirring, for 12 hours at a temperature of 40-45° C. and under a pressure of 5 mbar. Discharge of the filter delivered 7.4 kg of 99.2 GC % pure olfactory grade (−)-Ambrox in a 94 mol % yield based on the starting crude material.

The foregoing broadly describes certain embodiments of the present invention without limitation. Variations and modifications as will be readily apparent to those skilled in the art are intended to be within the scope of the present invention as defined in and by the appended claims.

The invention claimed is:

1. A method for purifying a crude flavor or perfumery or cosmetic ingredient or intermediate, wherein the crude flavor or perfumery or cosmetic ingredient or intermediate is in solid form, the method comprising:
   washing with an aqueous acid at a temperature less than the melting point of (−)-Ambrox;
   washing with an aqueous surfactant at a temperature less than the melting point of (−)-Ambrox; and
   washing with an aqueous alkali at a temperature less than the melting point of (−)-Ambrox:
   wherein the crude flavor or perfumery or cosmetic ingredient or intermediate is made by a bioconversion process, wherein the crude flavor or perfumery or cosmetic ingredient or intermediate is separated from a bioconversion broth prior to the method of purification; and
   wherein the method is a method for purifying crude (−)-Ambrox, crude (−)-Ambra-oxide, crude 3a-ethyl-6,6,9a-trimethyldodecahydronaphtho[2,1-b]furan, or crude (+)-Amberketal.

2. The method of claim 1, wherein the method comprises:
   (a) washing the crude flavor or perfumery or cosmetic ingredient or intermediate with the aqueous acid;
   (b) washing the product of step (a) with an aqueous alkali;
   (c) washing the product of step (b) with the aqueous surfactant.

3. The method of claim 1, wherein the aqueous acid is a weak acid and/or an organic acid and/or citric acid.

4. The method of claim 1, wherein the temperature of the aqueous acid ranges from about 17° C. to about 50° C.

5. The method of claim 1, wherein the aqueous alkali is a strong alkali and/or a hydroxide and/or sodium hydroxide.

6. The method of claim 1, wherein the temperature of the aqueous alkali is less than 70° C.

7. The method of claim 1, wherein the aqueous surfactant is an anionic surfactant.

8. The method of claim 1, wherein the temperature of the aqueous surfactant is less than 70° C.

9. The method of claim 1 further comprising one or more steps of washing with water prior to or after the washing with aqueous acid, the washing with aqueous alkali, and/or the washing with aqueous surfactant.

10. The method of claim 1, wherein all the washing steps take place in a single piece of equipment.

* * * * *